United States Patent
Jochumsen et al.

(10) Patent No.: US 8,216,524 B2
(45) Date of Patent: Jul. 10, 2012

(54) TESTING DEVICE FOR TESTING OR ANALYSING FLUIDS AND A HOLDER AND A STORAGE CONTAINER FOR SUCH DEVICES

(75) Inventors: Hans Henrik Jochumsen, Allerød (DK); Niels Stubager Frederiksen, Vanløse (DK); Janus Juul Rasmussen, Helsinge (DK); Thomas Nikolai Carlsen, Copenhagen V (DK)

(73) Assignee: Lattec I/S, Hillerod (DK)

( * ) Notice: Subject to any disclaimer, the term of this patent is extended or adjusted under 35 U.S.C. 154(b) by 1182 days.

(21) Appl. No.: 11/930,504

(22) Filed: Oct. 31, 2007

(65) Prior Publication Data

US 2008/0317635 A1  Dec. 25, 2008

Related U.S. Application Data

(63) Continuation of application No. 10/647,393, filed on Aug. 26, 2003, now abandoned.

(60) Provisional application No. 60/405,711, filed on Aug. 26, 2002.

(30) Foreign Application Priority Data

May 19, 2003  (DK) .......................... PA 2003 00751

(51) Int. Cl.
*G01N 21/01* (2006.01)
(52) U.S. Cl. ........ 422/401; 422/424; 422/429; 422/554; 422/560; 422/563
(58) Field of Classification Search .................. 422/424, 422/429, 430, 554, 560, 563
See application file for complete search history.

(56) References Cited

U.S. PATENT DOCUMENTS

| 4,142,863 A | 3/1979 | Covington et al. |
| 4,187,077 A | 2/1980 | Covington et al. |

(Continued)

FOREIGN PATENT DOCUMENTS

EP  0 511 120 A1  10/1992

OTHER PUBLICATIONS

PCT International Search Report in International Application No. PCT/DK/03/00560, mailed Mar. 29, 2004 (submitted in the parent U.S. Appl. No. 10/647,393).

(Continued)

*Primary Examiner* — Jan Ludlow
(74) *Attorney, Agent, or Firm* — Stephen A. Bent; Foley & Lardner LLP

(57) ABSTRACT

A testing device for testing or analysing fluids comprises a separately produced holder (10) and a sheet-or plate-like test member (11) including analysis reagent. The holder defines an abutment surface (13) for engaging with a side surface of the test member. Projections (15) formed on the holder are positioned and shaped so as to allow insertion of the test member into the holder by moving the test member into engagement with said abutment surface while engaging with opposite edge portions thereof. The projections may, for example, be tooth-shaped and have pointed ends, and at least some of the projections may have a leading edge (16) forming a ramp sloping towards a plane defined by the abutment surface so as to facilitate insertion of the test member into the holder. A stack of such testing devices may be arranged within a cassette from which they may be fed successively into an automatic analyser. The holder of the testing device may be re-used.

32 Claims, 20 Drawing Sheets

U.S. PATENT DOCUMENTS

| | | | |
|---|---|---|---|
| 4,230,757 A | 10/1980 | Toner | |
| 4,346,817 A | 8/1982 | Karcher | |
| 4,387,990 A | 6/1983 | Yazawa et al. | |
| 5,173,261 A | 12/1992 | Krause et al. | |
| 5,244,632 A | 9/1993 | Shaw et al. | |
| 5,256,372 A | 10/1993 | Brooks et al. | |
| 5,258,163 A | 11/1993 | Krause et al. | |
| 5,592,289 A | 1/1997 | Norris | |
| 5,599,505 A | 2/1997 | Fujisaki et al. | |
| 6,118,582 A | 9/2000 | Del Buono | |
| 6,287,783 B1 | 9/2001 | Maynard et al. | |
| 6,303,389 B1 | 10/2001 | Levin et al. | |
| 6,372,516 B1 | 4/2002 | Sun | |
| 2002/0102149 A1 | 8/2002 | Warhurst et al. | |

OTHER PUBLICATIONS

EP standard search report dated Jun. 12, 2003 in Application DK 2002 01254 (submitted in the parent U.S. Appl. No. 10/647,393).

Pawl-interacting shelf

TESTING DEVICE FOR TESTING OR ANALYSING FLUIDS AND A HOLDER AND A STORAGE CONTAINER FOR SUCH DEVICES

CROSS-REFERENCE TO RELATED APPLICATIONS

This application is a Continuation Application of U.S. application Ser. No. 10/647,393, filed Aug. 26, 2003 now abandoned, incorporated herein by reference, which claims the benefit of U.S. Provisional patent application Ser. No. 60/405,711, filed Aug. 26, 2002, and priority from Denmark Application PA 2003 00751, filed May 19, 2003.

The present invention relates to a testing device for testing or analysing fluids.

It is known to make qualitative or quantitative analytical determination of constituents of fluids, such as body fluids of humans or animals, for example milk, by using so-called test carriers. Test carriers are usually strip-, sheet- or plate-like members including porous or fibrous test layers with one or more chemical reactants or reagents. When a liquid sample to be tested is applied to the test carrier and comes into contact with the reagents therein a detectable signal, such as a colour change, is generated. Such signal can be evaluated visually or by means of a suitable testing or analysing apparatus. Usually, the test carrier (in the following also referred to as "test member") is mounted in a plastic holder or frame so that it can be handled properly in an analysing apparatus. Such known holders or frames are disclosed in i.a. EP-A-0 511 120, U.S. Pat. Nos. 4,230,757, 4,387,990, 5,173,261, 5,244,632, and 5,258,163.

Because the known holders or frames are usually made from two or more separate parts, which have to be interconnected when the test carrier or test member is mounted, mounting of the test members in the known frames or holders is relatively complicated and time consuming, and replacement of the test member so that the holder may be re-used, is normally not possible in practise.

Therefore, the present invention has for its object to provide a testing device and a holder or frame allowing a very simple and easy mounting of the test member in the holder or frame.

Thus, the present invention provides a testing device for testing or analysing fluids and comprising at least one strip-, sheet- or plate-like test member including analysis reagent and having opposite side surfaces surrounded by edge portions, and a separately produced holder having retaining means for receiving and retaining the test member in a predetermined relative position in the holder, said retaining means comprising an abutment surface engaging with one of said side surfaces of the test member, and projections, which are positioned and shaped so as to allow insertion of the test member into the holder by moving the test member into engagement with said abutment surface while engaging with opposite edge portions thereof.

The testing device according to the invention allows for a very simple and easy mounting of the test member in the holder by simply pushing the test member towards the abutment surface. While the test member is pushed into abutting engagement with the abutment surface the projections are engaging with opposite edge portions of the test member. Thus, the projections will either locally deform opposite edge portions of the test member and/or penetrate into the material of such edge portions, whereby the test member may be retained in the desired position in the holder. Because the inner side surface of the test member is in abutting engagement with abutment surface of the holder, the correct mutual position in the holder is secured. Also, after use the test member may rather easily be removed and replaced by a fresh one, so that the holder may be re-used, if desired.

In the present context the term "sheet- or plate-like test member" should comprise not only a test member made from two or more layers comprising i.a. porous materials and plastic films, laminates etc., but also test members in the form of strips or rods, which could have been made by cutting a sheet or plate into such strips or rods, and test members having varying thicknesses along at least one dimension.

Preferably, the projections are tooth-shaped with pointed ends, whereby the projections can better bite or penetrate into the material of the test member edge portions. Alternatively or additionally, each of at least some of the projections may have a leading edge forming a ramp sloping towards a plane defined by the abutment surface so as to facilitate insertion of the test member into the holder. When the test member is inserted into the holder and is pushed or biased towards the abutment surface of the holder, the edge portions of the test member will first meet the inwardly sloping ramp-like leading edge of the projections. The sloping leading edges of the opposite projections cause a slight lateral compression of the opposite edge portions of the test member so that these edge portions may partly or completely pass the free ends of the projections, which may be pointed. Additionally, the leading edge of the projections may form a cutting edge so that the sloping cutting edge may at least partly cut into the edge portion of the test member, when the test member is moved into engagement with the abutment surface.

In order to prevent the test member from moving unintentionally out of engagement with the abutment surface the leading edge of at least some of the projections may be barbed, and/or the trailing edge of the projection may be shaped so that the free end of the projection functions like a barb. Thus, the trailing edge may slope in the same direction as the leading edge and define with the abutment surface an acute angle, which is smaller than the acute angle defined by the leading edge. Alternatively, each of at least some of the projections may have a trailing edge extending substantially parallel with and spaced from a plane defined by the abutment surface. It is also envisaged that the trailing edge or surface slope in a direction opposite to the direction of the leading edge. In this case the free pointed end of the projection may still function as a barb, and the trailing edge or surface may function as a supporting surface abuttingly engaging with the adjacent side surface opposite to the abutment surface provided that the said spacing substantially corresponds to the thickness of the sheet- or plate-like testing member. In order to allow test members of different thicknesses to be safely retained in a holder, the projections of the holder may be positioned so as to be differently spaced from the plane defined by the abutment surface. It is also envisaged that the projections may be formed by thermoplastic deformation of wall parts of the holder prior to or after insertion of the test member in the holder.

The terms "leading edge" and "trailing edge" as used herein should be understood as the edge coming first and the edge coming last, respectively, into engagement with the test member, when the test member is moved into the holder.

In one of the preferred embodiments the holder is a channel-shaped member having an inner bottom surface defining said abutment surface and opposite inner side surfaces from which projections extend in opposite directions. A holder of this type is suitable for use in connection with an elongated test member of the "lateral flow stick" type, in which the fluid to be tested is supplied at one end of the elongated test member.

In another preferred embodiment the holder is frame-shaped and defines an opening therein, and the abutment surface extends around and adjacent to said opening. Because projections may be positioned all way around the opening through which the test member is exposed it is possible to obtain a very exact position of the exposed side surface part in relation to the holder.

In order to facilitate storing of a stock of testing devices, the holder preferably has upper and lower complementary surfaces so as to allow stacking of a plurality of testing devices on top of each other. Preferably, such complementary surfaces are shaped so as to allow mutual displacement of stacked testing devices in a direction transversely to the longitudinal direction of the stack. As shown in the Figures, the testing devices may be displaced along an axis transverse to the longitudinal axis of the stack, but are prevented from moving along other axes transverse to the longitudinal axis. As explained below, such features may be advantageous when the stacked testing devices are stored in a storage container or cassette from which they are dischargeable one by one.

The testing device may be used for testing of any type of liquid for which suitable test members of the type in question exist. In a presently preferred embodiment the testing device according to the invention is for use in colorimetric testing of milk.

According to a further aspect the present invention also relates to a holder for a testing device as that described above, said holder comprising means for receiving and retaining a sheet- or plate-like test member, which has opposite side surfaces surrounded by edge portions, in a predetermined relative position in the holder, said retaining means comprising an abutment surface for engaging with one of said side surfaces of the test member and projections, which are positioned and shaped so as to allow insertion of the test member into the holder by moving the test member into engagement with said abutment surface while engaging with opposite edge portions thereof.

In principle, the holder according to the invention may be composed by two or more separate parts. In the preferred embodiment, however, the holder is formed integrally, for example by injection moulding or extrusion from plastic material.

The testing devices are suitably delivered to the user in a storage container or cassette, which may be connected to an analyser, and from which a testing device may be withdrawn one by one when needed. Even though the testing devices are usually fed into an automatic analyser, they may be discharged from the container or cassette manually. Usually the testing devices are disposed with after use. However, it is possible to remove the test member from the holder after use and to reuse the holder.

Thus, the invention also relates to such an elongated storage container or cassette for receiving a plurality of stacked testing devices of the type having at least one sheet- or plate-like test member including analysis reagent, and a holder receiving and retaining the test member in a predetermined relative position in the holder, said container comprising a movable support member for supporting a lower testing device in said stack, an upper abutment surface for engaging with an upper testing device in the stack, a discharge opening aligned with said upper testing device, so as to allow discharge of said upper testing device by displacing the same along said abutment surface. The movable support member may be biased towards the upper abutment surface, for example by means of a spring positioned in the lower part of the container or cassette. In the preferred embodiment the biasing means is part of the analyser, such as a piston or plunger moving trough an opening in the bottom part of the cassette.

In the latter case it is necessary to prevent that the movable support member moves in a direction away from the upper abutment surface, when the container or cassette is removed from the analyser and its biasing means. Therefore, the storage container preferably further comprises one-way means associated with the movable support member allowing the movable support member to move in a direction towards the upper abutment surface, only. These one-way means may, for example, comprise at least one succession of teeth, such as a rack or ratchet teeth, and at least one pawl member co-operating therewith.

Such a ratchet system may retain the support member in a plurality of positions being longitudinally spaced corresponding to the pitch of the succession of teeth. In order to increase the number of longitudinal positions, in which the support member may be retained for a given pitch of the rack or succession of teeth, the one-way means may comprise at least two pawl members, which are connected to the supporting member for co-operating with a succession of teeth formed on an inner side surface of the storage container, the free ends of the pawl members being spaced in the longitudinal direction of the container by a distance being different from a multiple of the pitch of the succession of teeth, preferably smaller than said pitch. Thus, if said spacing is for example half the pitch a number of the uniformly longitudinally spaced positions being the double of the number of teeth in the row or succession of teeth is obtainable.

According to a further aspect the invention also relates to a cartridge for receiving, storing and unloading a plurality of stacked testing devices, wherein the cartridge comprising a housing defining an internal passage for said stack of sticks, and wherein the housing comprising: a lower charge opening for receiving said stack of testing devices, a support member for supporting a lower testing device in said stack, an upper abutment surface for engaging with an upper testing device in the stack, and an upper discharge opening, substantially aligned with said upper testing device, so as to allow discharge of said upper testing device by displacing the same along said abutment surface.

The housing of the cartridge may be assembled by two halves, together defining oppositely side surfaces, and a front and a back surface. And wherein the two halves are detachable or non-detachable assembled.

The cartridge further comprising a discharge opening which comprises guiding trails or incisions for guiding a testing device upon discharging.

The inside of the side surfaces of the cartridge may comprise guiding trails for guiding a stack of testing devices through the passage. The side surfaces further comprise at least one serrated track on the inside, forming one side of an internal one-way stair for a movable support member. The movable support member is movable in relation to the housing.

The one-way stair inside the cartridge allows the movable support member to move in a direction towards the upper abutment surface, only. The one-way means comprise at least one succession of teeth, such as a rack or ratchet teeth, and at least one pawl member co-operating therewith.

The invention further relates to a cartridge comprising at least two pawl members, which are connected to the supporting member for co-operating with a succession of teeth formed on an inner side surface of the storage container, the free ends of the pawl members being spaced in the longitudinal direction of the container by a distance being different from a multiple of the pitch of the succession of teeth, preferably smaller than said pitch.

The cartridge further comprises a locking device in the vicinity of the discharge opening on at least one of the side surfaces, for preventing unintentional discharges of testing devices. The locking device comprises at least one flexible protrusion obstructing at least a part of said discharge opening.

The invention further relates to a load device for loading a stack of testing devices into a cartridge, the load device comprising: a base member, a first and a second column oppositely arranged and extending upwards from said base member, and being adapted to receive and hold one or more testing devices there between, and a lifting device for slidably lifting one of more testing devices along said columns. Each column comprises a groove for receiving and guiding an end of a test stick. The lifting device comprises a handle for manually sliding said lifting device along said columns. The lifting device is preferably automatically slid along said columns. The lifting device further comprises a support surface for supporting at least a part of the lower testing device in said stack of testing devices.

The movable support member is preferably arranged between said support surface of the lifting device and the lower most testing device in the stack.

In order to facilitate the guiding of the lifting device, the device comprises guiding means abutting a side portion of said columns so as to guide the device along the columns.

The invention further relates to a method for loading a plurality of testing devices into a cartridge by using a load device, the load device comprising: a base member, a first and a second column oppositely arranged and extending upwards from said base member, and being adapted to receive and hold one or more testing devices there between, and a lifting device for slidably lifting one of more testing devices along said columns.

the method comprising the steps of: stacking one or more testing devices between the columns, guide an empty cartridge from above the columns and down towards the base member, lifting the lifting device in order to push the sticks upwards until the upper most testing device abuts an upper abutment surface of said cartridge, removing the cartridge loaded with the sticks from said load device.

The method may further comprise, prior to the step of placing testing devices, the step of placing a support member between the columns for supporting and holding the stack of testing devices inside said cartridge upon removing the loaded cartridge.

BRIEF DESCRIPTION OF THE DRAWINGS

The invention will now be explained with reference to the drawings illustrating embodiments of the testing device, the holder and the storage container according to the invention, and wherein:

FIG. 28*a* is before assembly and the right FIG. 28*b* is after assembly.

FIGS. 1-3 illustrate a first embodiment of a testing device according to the invention comprising a holder 10 and a sheet- or plate-like test carrier or test member 11, which is a sheet or plate member containing for example colorimetric reagents. The holder 10, which may be made from plastic material by injection moulding, and the test sheet member 11 are produced separately and usually at different locations. Therefore, before the testing device may be used the test sheet member has to be mounted in the holder 10.

Figure 1:
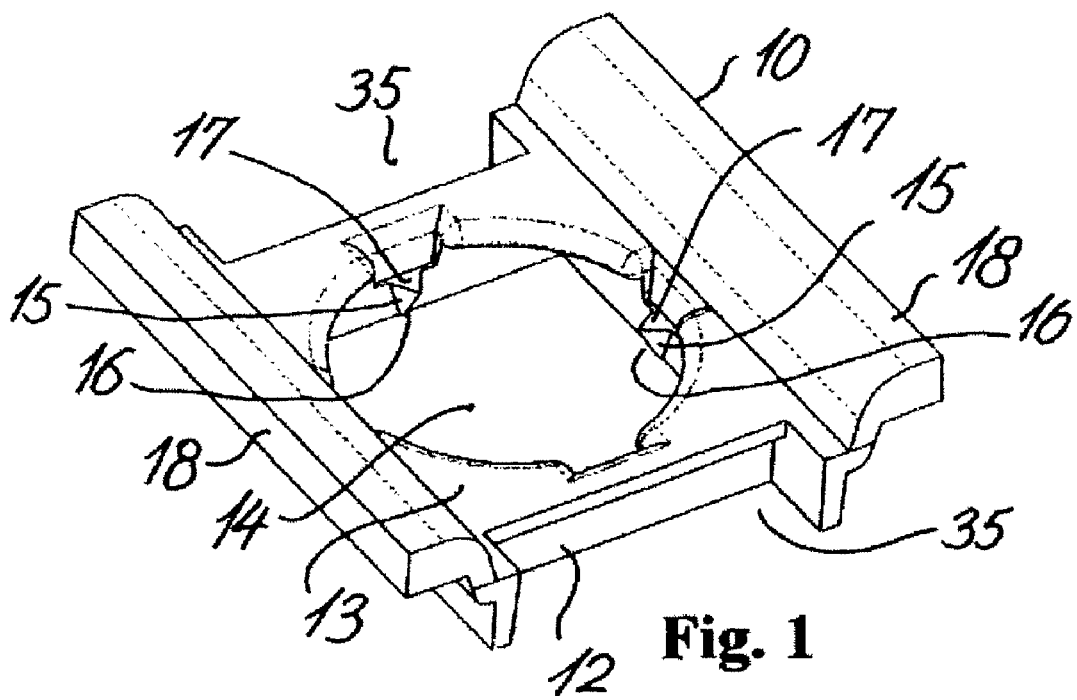
FIG. 1 is a top perspective view of a first embodiment of a holder according to the invention for a testing member.
Figure 2:
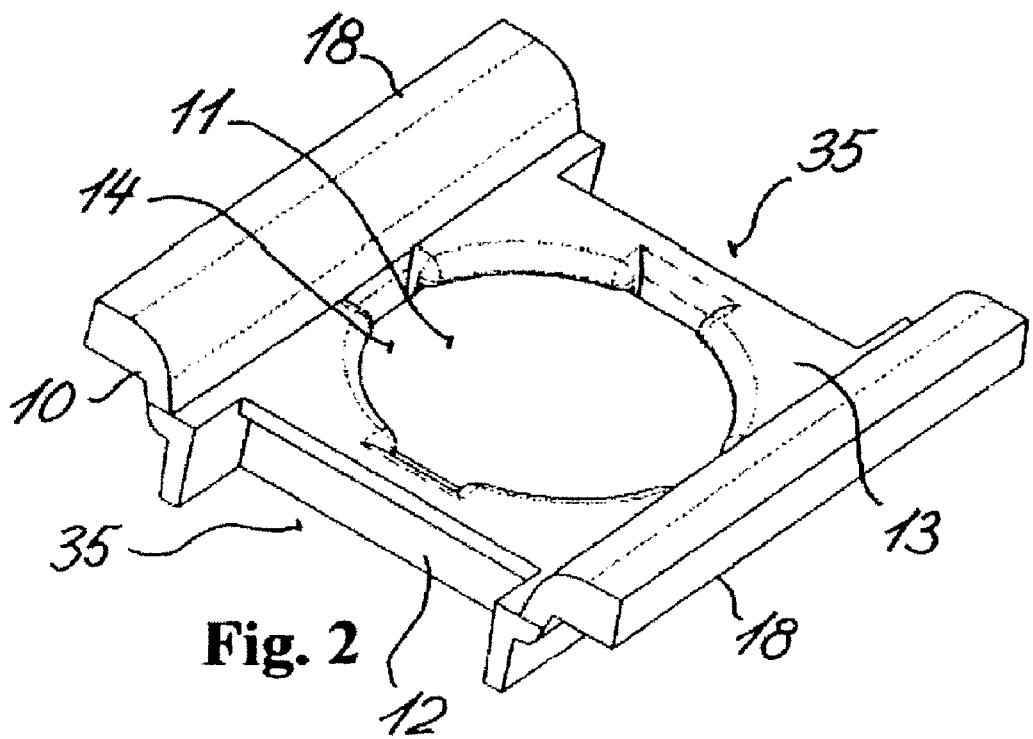
FIG. 2 is a top perspective view of a first embodiment of the testing device according to the invention comprising the holder shown in FIG. 1.
Figure 3:
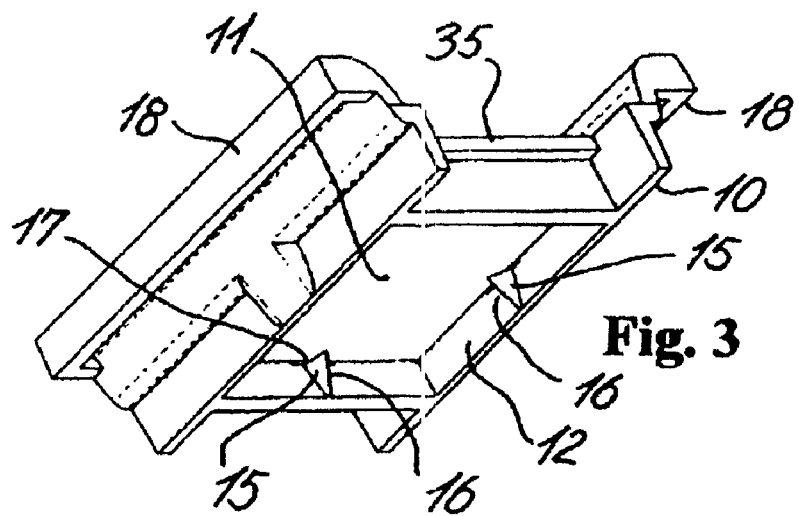
FIG. 3 is a bottom perspective view of the testing device shown in FIG. 2.

The holder 10 shown in FIGS. 1-3 comprises a substantially rectangular frame 12 having inner side walls defining a passage having a cross-section corresponding to the size and shape of the test member 11. The upper end of the passage defined by the frame 12 is partly covered by an upper wall 13 defining an exposure opening 14 therein. The bottom surface of the upper wall 13 defines an abutment surface for the sheet-like test member 11 when mounted in the holder 10.

Oppositely arranged inner side wall parts have tooth-like projections 15 formed thereon. Each projection has a sloping leading edge 16 and a support surface or trailing surface 17, which is opposite to and substantially parallel with the bottom surface of the upper wall 13. Wing-like flanges 18 extending outwardly from opposite sides of the rectangular frame 12 are used for guiding the testing device along a path of movement or processing path in an automatic analyser, not shown.

A plate or sheet-like test member 11, such as a sheet of chemistry paper with a thickness of about 0.4 mm, may be mounted in the holder shown in FIG. 1 simply by pushing the test member upwardly trough the frame 12 towards the bottom side of the upper wall 13. The edge portions of the sheet-like test member 11 thereby come into engagement with the leading edges 16 of the projections, whereby these edge portions are locally compressed. Preferably, the thickness of the test member 11 corresponds to the axial distance between the abutment surface formed by the bottom surface of the upper wall 13 and the opposite supporting surfaces 17 of the projections 15. In such case the test member may be safely retained in position in the holder 10 between the bottom surface of the wall 13 and the opposing supporting surfaces 17 of the projections 15. When the testing device has been introduced into an analyser a liquid sample to be tested may be applied to the surface of the test member 11 exposed in the opening 14, and a colorimetric reaction may be read by the analyser and translated into a test result.

Figure 17:
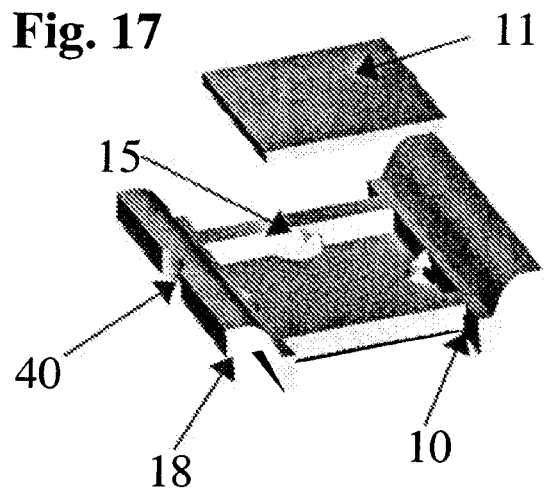
FIG. 17 is a top perspective view of the fourth embodiment with a test stick above.
Figure 20:
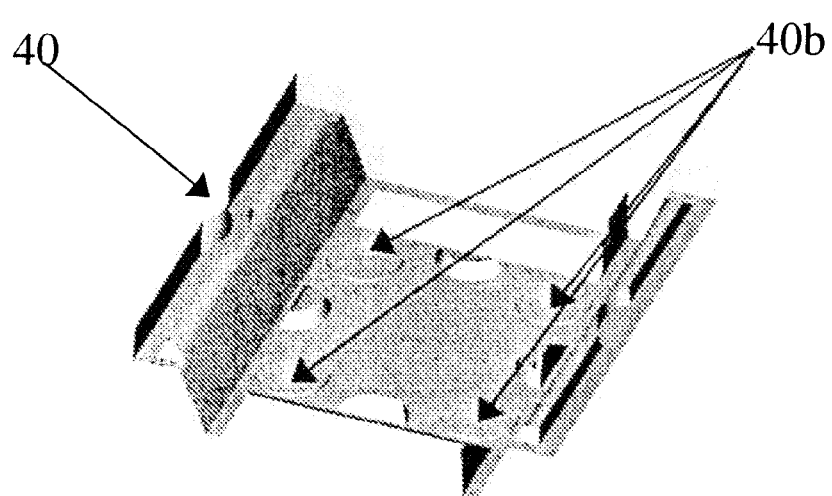
FIG. 20 is a bottom perspective view of the fourth embodiment according to the invention, showing the point of injection and the marks from the ejection pins.

FIG. 17 illustrates another embodiment of the testing device according to the invention. This embodiment comprises an upper side and a lower side in relation to an analysis instrument. The flanges 18 are positioned on the upper side of the holder and the retaining means are positioned and shaped so as to allow insertion of a plate or sheet-like test member 11, such as a sheet of chemistry paper, from the upper side of the holder (which is the opposite direction compared to the loading of a test member in the embodiment of FIG. 1). FIG. 20 shows the same embodiment from the lower side.

Figure 4:
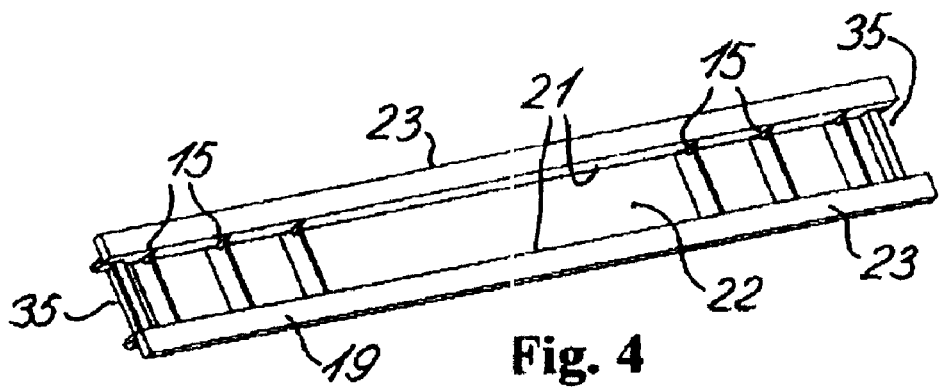
FIG. 4 is a top perspective view of a second embodiment of a holder according to the invention.
Figure 5:
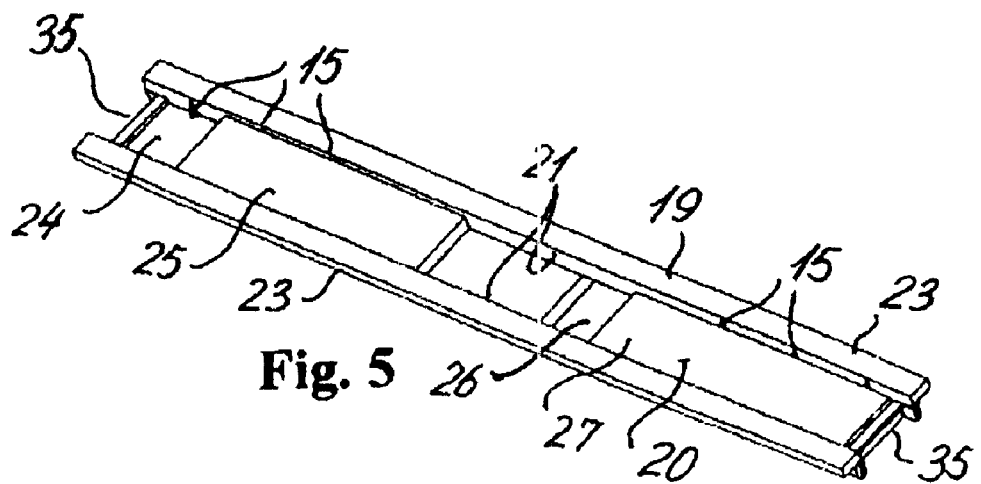
FIG. 5 is a top perspective view of a second embodiment of the testing device according to the invention comprising the holder shown in FIG. 4.

FIG. 5 illustrates another embodiment of the testing device according to the invention comprising a channel-shaped holder 19 shown in FIG. 4 and an elongated strip-type test member 20 having varying thicknesses along its length. The channel-shaped holder 19 has a pair of opposite side walls 21 and a connecting bottom wall 22 defining an inner abutment surface corresponding to the bottom surface of the upper wall 13 in the embodiment described above in connection with FIGS. 1-3. A number of tooth-like projections 15 corresponding to those described above in connection with FIGS. 1-3 are formed on the opposite inner surfaces of the side walls 21. A pair of oppositely directed flanges 23 extends from the upper edges of the side walls 21 and serves as guide flanges when the testing device is processed in an analyser.

As shown in FIG. 5, the lateral stick or test member 20 comprises various longitudinal sections including various layers and being of different thicknesses. These sections may, for example, include an application section 24 to which a liquid sample to be tested may be applied, a transfer section 25 for adding selected chemicals to the liquid sample and for transferring the same to a reading section 26 at which a colorimetric reaction may be read by an automatic analyser, and a collecting section 27 for receiving the liquid sample. Therefore, the various sections of the stick or test member 20 have different thicknesses. As apparent from FIG. 5 the thickness of the application section 24 substantially corresponds to the distance between the abutment surface defined by the bottom 22 and the supporting surface 17 of the adjacent projections 15, while the thicknesses of sections 25 and 27 substantially exceeds that distance. This means that the projections 15 adjacent to the sections 25 and 27 bite into the edge portions of these sections and thereby retain them in the desired position in relation to the holder. Preferably, the distance between the abutment surface defined by the bottom 22 and the supporting surface of the projections 15 correspond to the thickness of the bottom layer of all of the sections 24-27.

Figure 23:
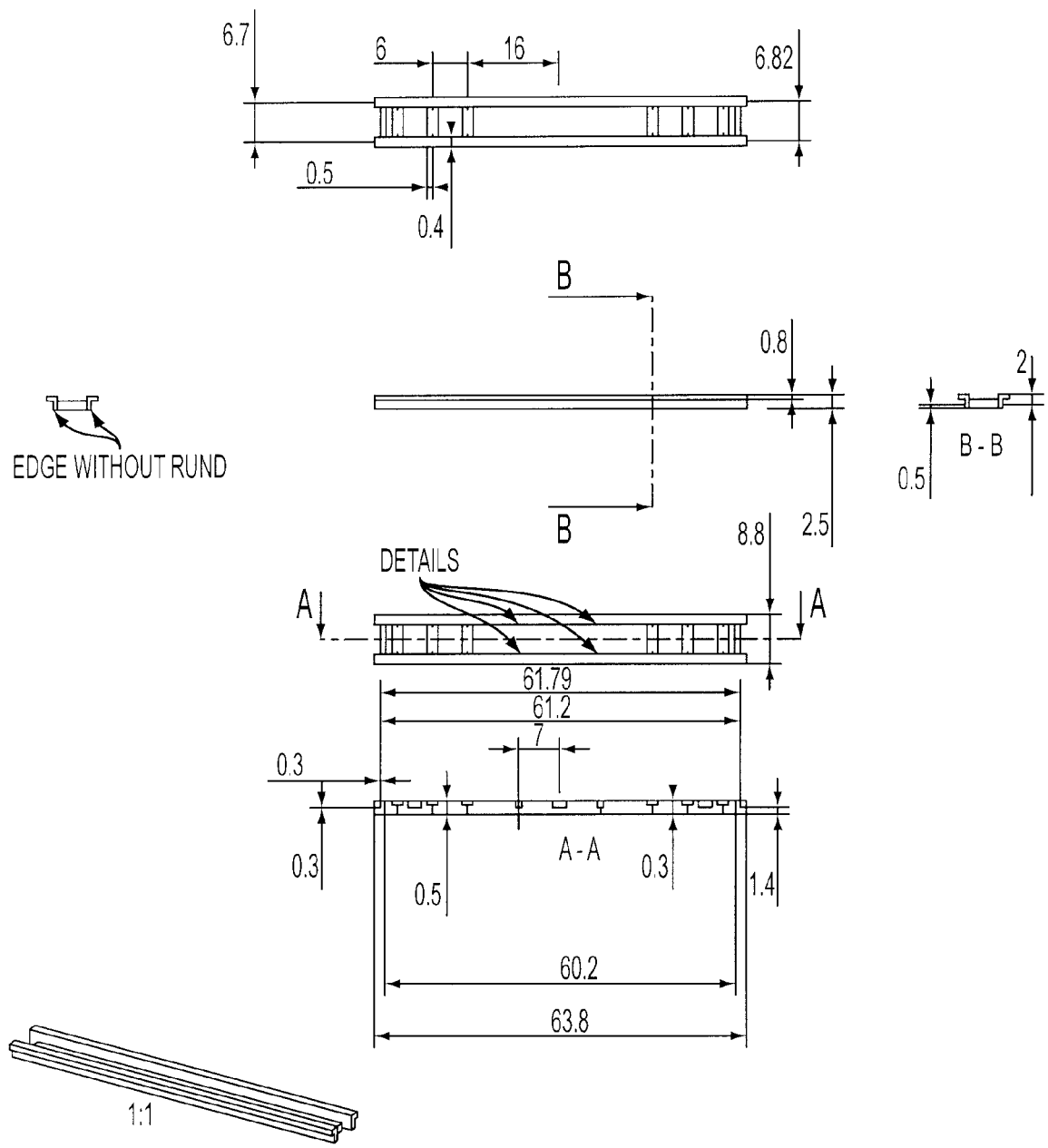
FIG. 23 shows the drawings of the third embodiment.
Figure 24:
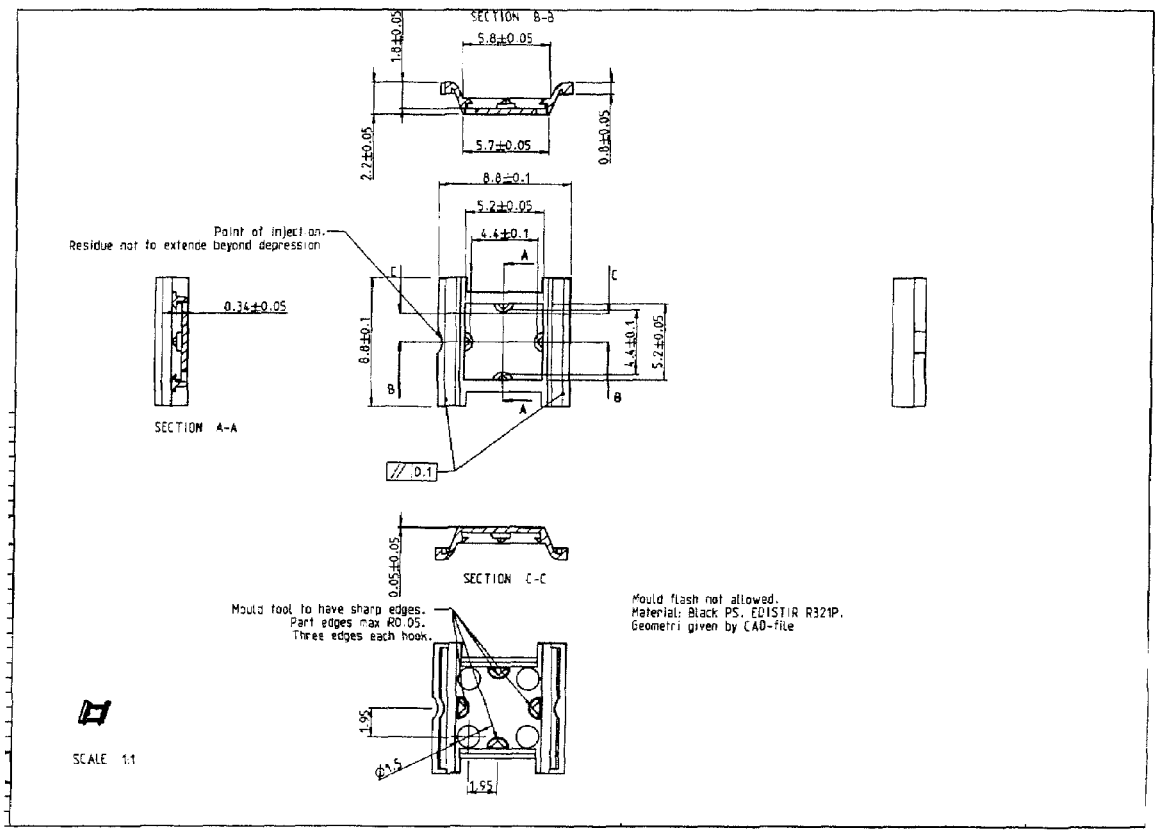
FIG. 24 shows the drawings of the fourth embodiment.

The stick frames shown in FIGS. 23 and 24 provide and facilitate handle-ability to the chemistry pad.

The life cycle of a frame from production to waste is described below: Firstly the frame is manufactured by injection moulding. There after the chemistry pad is pressed into the frame thus assembling the chemistry pad and frame, now forming a dry stick [DS], shown in FIG. 12 and FIG. 18. The dry sticks are stacked in appropriate numbers and inserted in to a cartridge. A formed sheet of preferably stainless steel is inserted under the stack forming a no-return floating bottom, securing the stack at any stack height, shown in FIG. 36. When the cartridge and the dry sticks have been assembled the cartridge is wrapped in protecting seam-welded bags, packaged in boxes and put on stock, while kept cold at 5° C. Thereafter the box is transported and distributed to the end-user, still kept cold. When the box arrives to the end-user, the end-user also have to make sure that the boxes containing the cartridges are stored in a cold storage such as a refrigerator. Single cartridges are retrieved from the cold storage and brought to the analysis instrument and inserted in the storage.

The chemistry has two formats, lateral (LS) flow and colorimetric (CS):

The lateral flow chemistry consists of a bottom foil with nitrocellulose and glue on which dosage, reaction and suction fiber pads are placed. A tape is placed on top, except at the dosage area. The chemistry is 5 by 60 mm and up to 1.6 mm high. The position of the reader-line is approximately in the middle. Preferably somewhere between 25 mm and 39 mm such as 34 or 35 mm from the leading edge.

The colorimetric chemistry is formed by a 5 by 5-mm fiber-pad. The pad is approximately 0.34-0.6 mm thick.

The material preferably used in the manufacturing of the frames is Polystyrene [PS]. It has been chosen as it has a low cost per volume and a high stiffness modulus. Furthermore it has a high surface tension towards milk, higher than Polyethylene [PE], reducing the risk of the milk seeking out in the gap between frame and chemistry.

The frame are preferably injection moulded. The geometry can be realized in injection tooling, without complexity e.g. separately moving cores etc. Due to the waste numbers needed, the production tooling will have several cavities—maybe as many as 64, and will utilize hot-runners and micro injection-nozzles. The tooling produce no runners and inlet-parts, meaning that there is need to separate and recycle scrap.

The point of injection is placed in an indention of the geometry to allow some degree of undefined geometry, see FIG. 20.

The ejection pins are slightly prolonged, 0.05 mm, so that wear and tolerances can be taken-up without causing protrusions on the frame.

The stick assembling equipment checks each frame for faults, e.g. dimensions exceeding tolerances and incomplete geometry, and expels faulty frames. This could be done utilizing vision systems and/or laser grids.

The chemistry paper is mounted in the frame simply by a pressing motion with an appropriate shaped plunger. No-return hooks (15) placed on the walls of the frame secure the chemistry by positive engagement, shown in FIGS. 1 and 4.

The bottom plastic foil of the lateral chemistry flips under the hooks, although it has cut/deformed to some degree. Frames were realized in soft tooling and assembly of chemistry carried out. It was found that the chemistry at the reader-line did not relate to the bottom of the frame as it bended, which affects the focus/precision of the reader. Therefore rib-protrusions 15a are added, which have a transversal distance smaller than the width of the chemistry, thus retaining the pad.

The colorimetric fiber pad is partly formed around and under the hooks, thus retained inside the holder.

The first embodiment of the colorimetric frame, had the chemistry inserted from underneath see FIGS. 1 and 2. This design presents the top of the chemistry with less tolerance of the level, and has a higher flexibility regarding different/changing pad thickness and less critical retaining function, as the hooks have a better leading angle. The second embodiment of the colorimetric frame, shown in FIGS. 17 and 18 may be preferred if the concept of dosage is positive contact of the dosage device to the chemistry instead of a non-contact of the dosage device. A positive contact concept of the dosage device calls for support from underneath of the pad.

Thus, the advantages of having a frame loaded from beneath, shown in FIGS. 1 and 2, is that the distance to a reader (not shown) is not dependent on the thickness of the chemistry.

Figure 18:
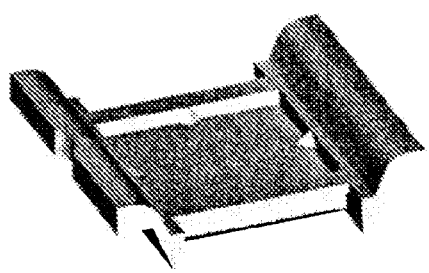
FIG. 18 is a top perspective view of the fourth embodiment loaded with a test stick.
Figure 19:
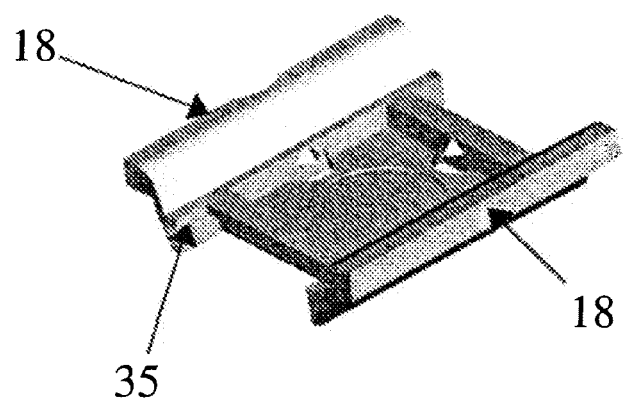
FIG. 19 is a top perspective view of the third embodiment of an empty holder according to the invention.

The advantages of having a frame loaded from above, shown in FIGS. 17 and 18 is that the method of applying fluid on to the chemistry can be done by direct contact. Because the chemistry is resting against the bottom of the frame it is not removed when the application tool apply a force on to the chemistry.

The design of the frames aim to have:
Lowest possible cost
Ease of automated production
High reliability of AI—avoid malfunctions and influence of the precision of measurements
Small physical dimensions
Ease of disposal
Lowest possible environmental impact
Ease of development, same design paradigm for both frames
Same level of dosage for both DS
Same level of reading for both DS The overall height, is preferably 2.5 mm, of the LS frame, and may be determined by the chemistry used in the LS—the chemistry is preferably 1.6 mm thick. The floor of the LS-frame is preferably 0.6 mm thick, leaving a clearance of preferably 0.3 mm from the top of the frame to the chemistry. The stack-height of the LS is the full 2.5 mm.

The stack-height of the CS may be reduced to 1.4 mm, by preferably reducing the thickness of the frame body, utilizing the thinner chemistry. The overall height of the CS frame is preferably 2.2 mm. The height of the CS-frame is based on the distance from the upper side of the LS frame to the LS-read plan. Furthermore is the height of the CS-frame also depending on the thickness of a CS-stick and the thickness of the floor of the CS-frame.

Figure 6:
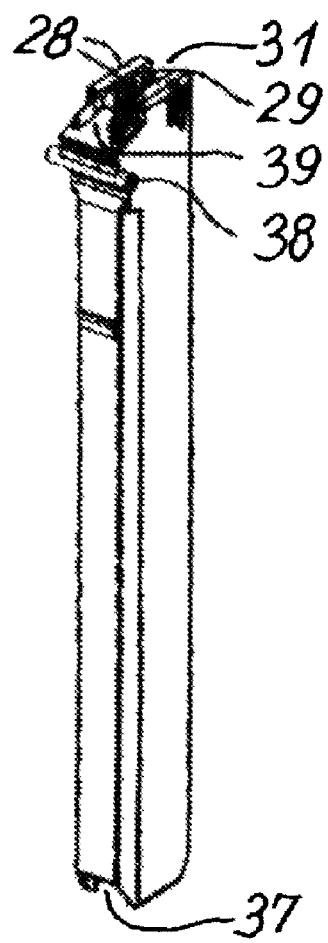
FIG. 6 is a perspective view of a first embodiment of a storage container or cassette according to the invention for receiving a stack of testing devices as that shown in FIGS. 2 and 3.
Figure 7:
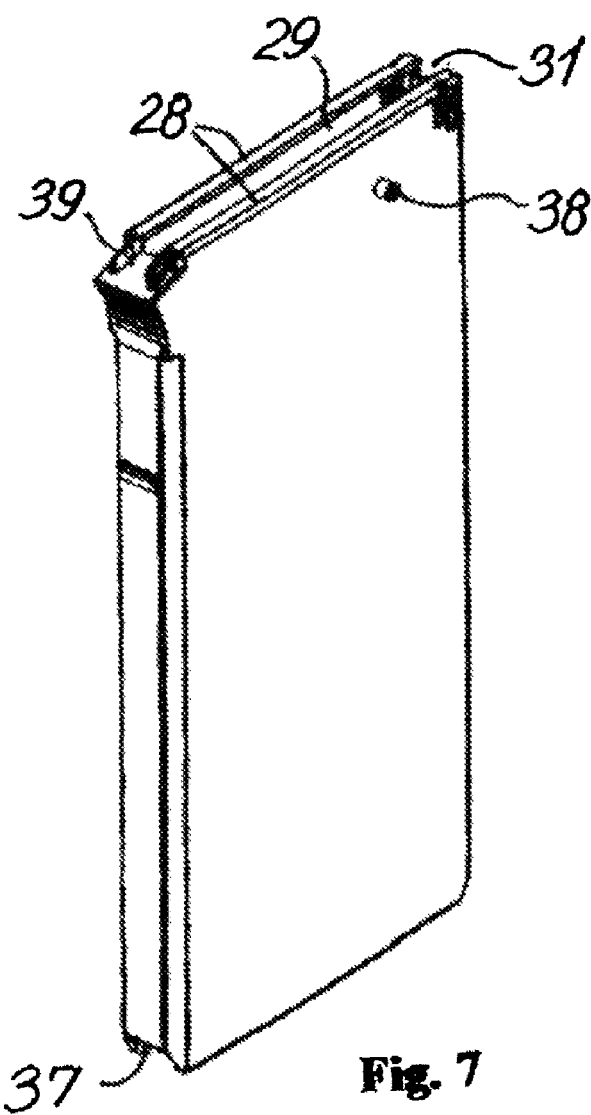
FIG. 7 is a perspective view of a second embodiment of a storage container or cassette according to the invention for receiving a stack of testing devices as that shown in FIG. 5.
Figure 8:
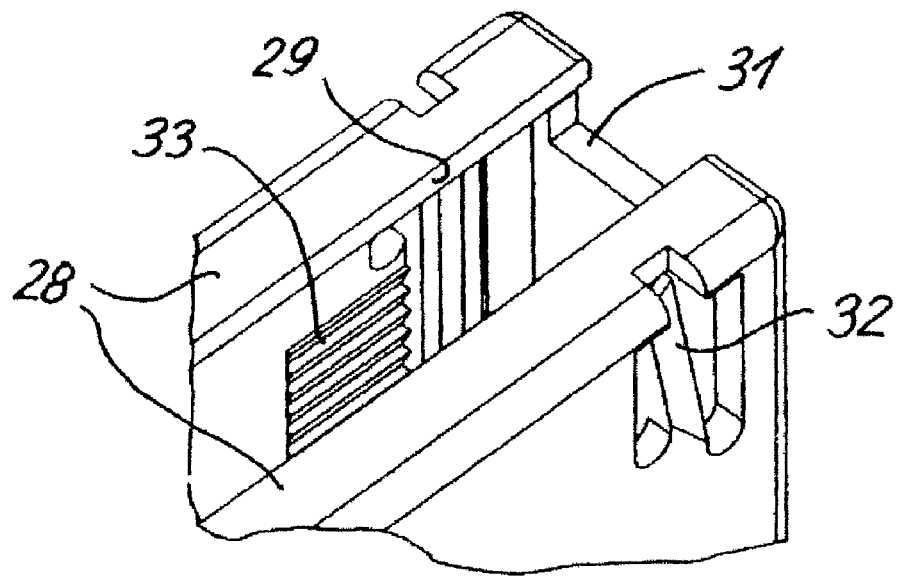
FIG. 8 is a fragmentary perspective view of an upper part of the storage container or cassette of FIG. 7 shown in an enlarged scale.
Figure 9:
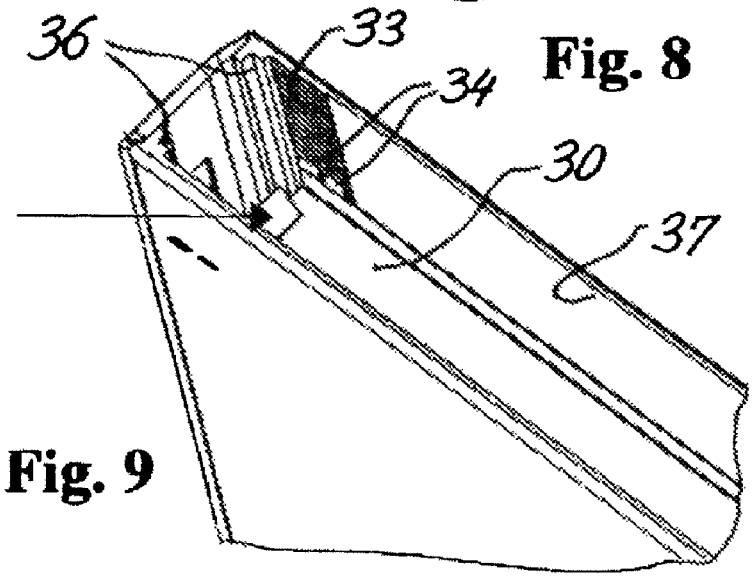
FIG. 9 is a fragmentary perspective view of a lower part of the storage container or cassette of FIG. 7 shown in an enlarged scale.

FIGS. 6 and 7 illustrate storage containers or cassettes for containing a stack of testing devices of the type shown in FIGS. 1-3 and 4-5, respectively. These cassettes are adapted to be mounted in an automatic analyser (not shown) so that the testing devices contained therein may be selective discharged for being processed in the analyser. Each of the cassettes shown in FIGS. 6 and 7 has a tubular shape with an inner rectangular cross-section substantially corresponding to the outline of the testing devices to be housed therein (FIGS. 2 and 5, respectively), and an open bottom or bottom opening 37 as shown in FIG. 9. The upper end of each of the storage containers or cassettes shown in FIGS. 6 and 7 is partly covered by a pair of opposite, substantially parallel flanges or ledges defining a transversely extending space 29 there between (FIG. 8).

It is important that colorimetric as well as lateral sticks are guided securely and that they are as easy to handle as possible all the way from production until use in the analysis instrument.

The vertical guidance has to be so robust that the sticks are not erroneously oriented, before they are taken out by the stick mover horizontally. It is necessary for the cartridge to be designed in a way that enables the stick mover to run into an integration surface and be presented to sticks in the same way each time.

During production, transportation and handling of the cartridge with sticks, the cartridge has to be able to withstand all possible ways of treatment, which may include pushes, strokes and even drops, but which must not make the sticks to be erroneous oriented. The LC (lateral cartridge) preferably contains 50 sticks, and the CC (colorimetric cartridge) preferably 100 sticks.

Due to various physical designs of colorimetric and lateral sticks, two types of cartridges are available. The two types are called Colorimetric Cartridge [CC] and Lateral Cartridge [LC], respectively. Apart from the depth, the two cartridges are almost identical. The two cartridges can be seen in FIG. 25 and FIG. 26.

Preferably a cartridge consists of two injection-moulded shells, which preferably have been ultrasonic welded together. The shells are preferably made of impact modified Polystyren, which has been chosen due to the favourable price and the mechanical qualities desired, both regarding strength/stiffness and welding.

In the following, the cartridge and the parts, which are integrated in the cartridge, are described more closely and will apply for both the CC and the LC.

Figure 27:
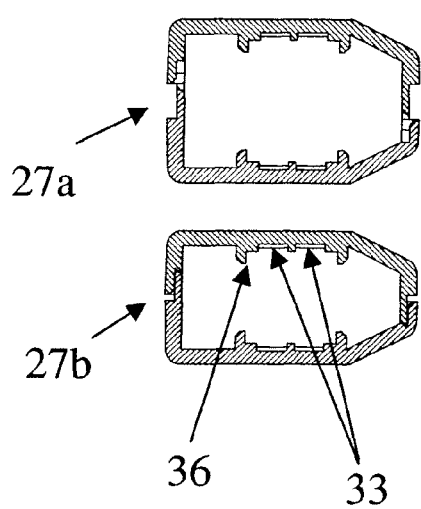
FIG. 27 shows a cross-section of a cassette before assembly 27*a* and after assembly 27*b*.
Figure 28:
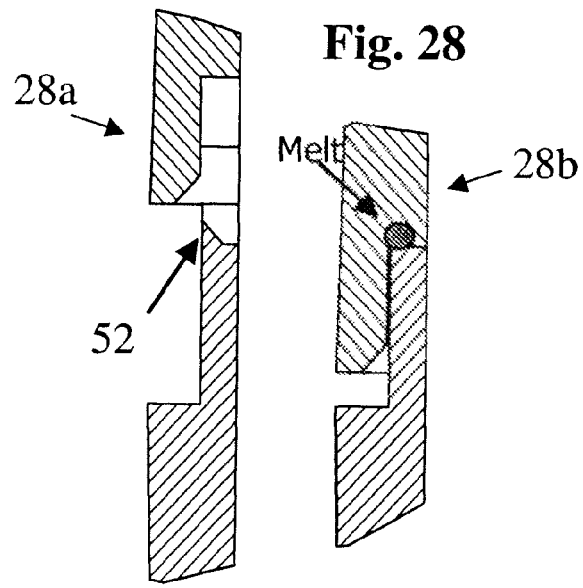
FIG. 28 shows a magnification of the assembly points in picture 28, the left

A cartridge preferably consists of two injection-moulded shells/sides, which preferably have been ultrasonic welded together, see FIGS. 27 and 28.

Figure 29:
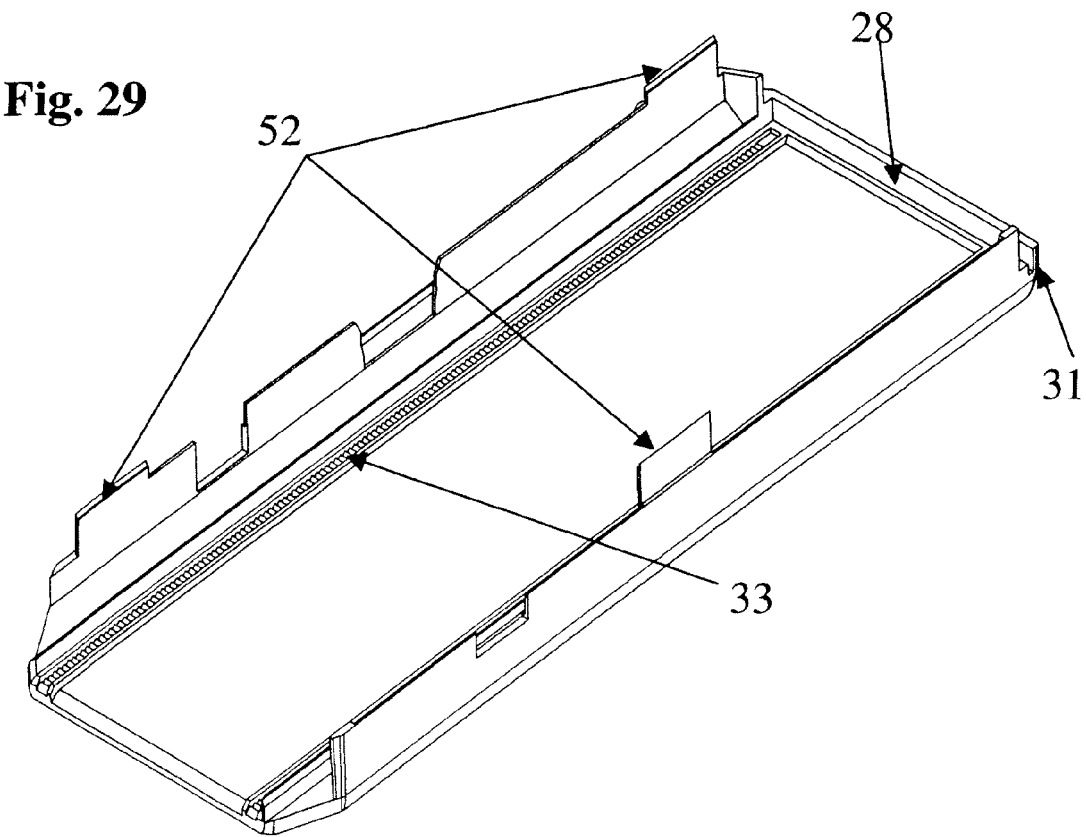
FIG. 29 shows the energy directors on one of the halves of a cartridge.

Each shell has three energy directors, see FIG. 29 (six per cartridge), which have been placed male/female alternately.

The welding takes place by way of a specially manufactured welding horn and a fixture on a 20 kHz welding machine.

The welding time including fixing time is preferably approx. 1.5 second.

In the production the welding may take place fully automated inline with an injection-moulding machine.

Each cartridge comprises a vertical guide-way for guiding sticks within the cartridge. Preferably the nominal air around the stick is 0.15 mm all the way round (thus 0.3 mm in each direction). The width of the guide in the edge is preferably 1.2 mm. See FIG. 31.

To make sure that the sticks can be handled smoothly without being squeezed by the cartridge and without capsizing (lateral sticks may have a tendency of that), the welding has to be as precise as possible.

Furthermore, each cartridge preferably comprises a spring lock in order to ensure that the sticks cannot be removed from the cartridge in case of shocks when handling, in such cases the sticks are held back by a spring lock built into the cartridge. Shown in FIGS. 32 and 33.

The blocking of the spring locks can preferably only be removed, when the stick is taken out of the stick mover.

Below follows some data and specifications of the cartridges. The cartridges are preferably welded in impact modified Polystyren. Some of the advantages of using Polystyren as material are because the Polystyren has good mechanical properties and is suitable for ultrasonic welding and it is also an Inexpensive material.

Figure 10:
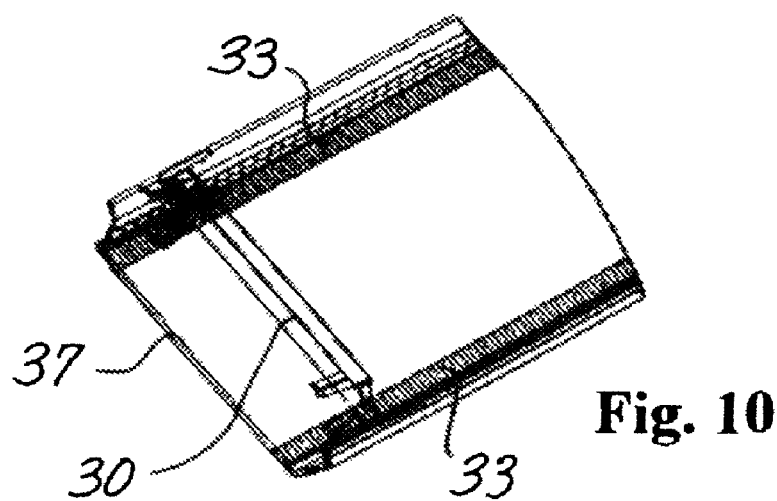
FIG. 10 is a fragmentary sectional view of the lower part of the storage container or cassette of FIG. 7 taken along a median plane of the container.

The preferred physical data for a Lateral Cartridge are:
Volume: 2×21500 mm$^3$
Weight: 2×22.6 g
Main dimensions (L×W×D): 160×13.2×25 mm And the preferred physical data for a Colorimetric Cartridge are:
Volume: 2×8200 mm$^3$
Weight: 2×8.6 g—Main dimensions (L×W×D): 160×13.2×25 mm To ensure that the sticks in the cartridge are always in the top of the cartridge, and that the stack of sticks is kept in place, the movable bottoms shown in FIG. 36 have been used. As shown in FIGS. 9 and 10, each of the storage containers or cassettes contains a movable bottom plate or support plate 30 and when loaded with a stack of testing devices (FIGS. 2 and 5) such stack is arranged between the bottom plate 30 and the inner surfaces of the flanges 28, so that the uppermost testing device in the stack is in abutting engagement with the flanges 28 and aligned with a discharge opening 31 formed in the adjacent cassette wall. A resilient finger 32 formed integrally with the cassette wall is frictionally engaging with the uppermost testing device in the stack so as to avoid unintentional discharge of the same trough the discharge opening 31. Rows of teeth or ratchet teeth 33 formed on opposite inner walls of the storage container or cassette are engaging with pawl members 34 (FIG. 9) connected to the movable bottom plate 30 so as to allow movement of the bottom plate 30 in one direction, only, namely towards the flanges or ledges 28.

The movable bottom 30 may be made of bent sheet metal, so that its shoulders are flexible and act as a lock. The lock runs against four internal one-way stairs in the cartridge (see illustration in FIGS. 37 and 38).

The movable bottom may be made of stainless steel preferably by way of laser cutting and bending.

When the cartridge has been emptied for sticks, and the bottom is in the top of the cartridge, a bend preferably approximately 45-degrees 44, ensures that a stick mover pawl will slide over the bottom. The bottom is guided between the four legs 43 and the side-guidance of the stairs shown in FIG. 38.

Some data and specifications for the movable bottom are described below. The movable bottoms are preferably made out or 0.10 mm stainless spring steel, AISI 301. The bottoms are first cut by laser cutting/photo etching items for function models. There after they are bent into the final shape by specially manufactured tools.

Figure 36:
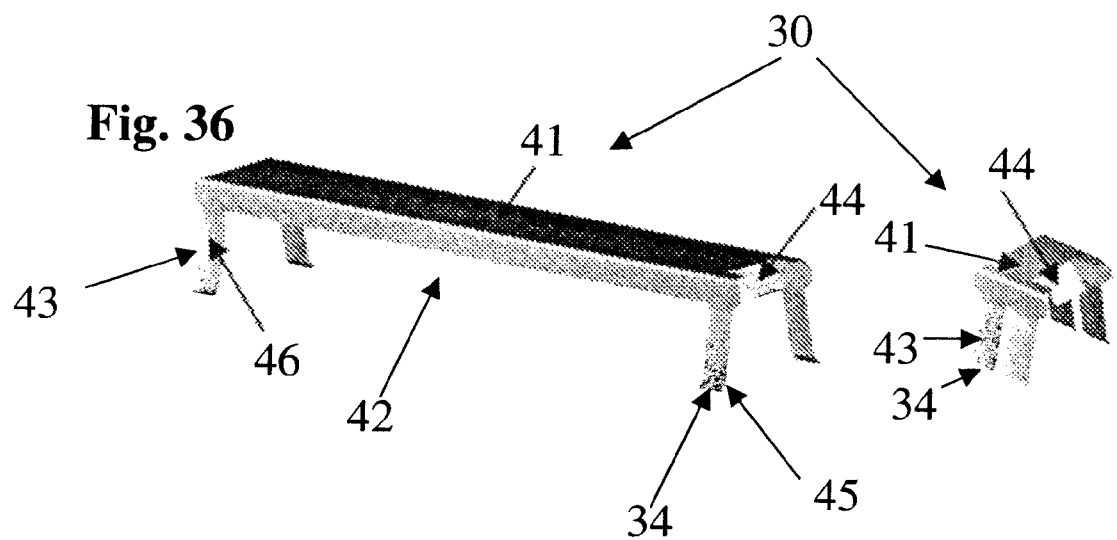
FIG. 36 shows two embodiments of the movable bottom plate.

Thus, the preferred method for making a movable bottom device comprises the steps of;
laser cutting (small batches) or punching (large batches), and
bending sheet metal The movable bottom device shown in FIG. 36 comprises a testing device support side 41, a plunger abutment side 42, and at least two legs 43.

The movable bottom device further comprises a slope 44 characterised in that a part of the support surface slopes downwards in relation to the stick support side, for guiding a testing device remover pawl.

The legs of the movable bottom device comprise at least one curvature 45 creating a base area 46 and a pawl 34.

The base area 46 is the part of the leg being close to the support surface, whereas the pawl area 34 is the part of the leg that is on the opposite side of the at least one curvature in relation to the base area. The pawl area being in a different angle in relation to the rest of the leg.

Preferably, at least two pawl members 34 differing in length are associated with each row of teeth 33, and said difference in length is smaller than the pitch of the row of teeth 33, preferably half the pitch or the pitch divided by the number of pawl members for each row of teeth, if more pawl members are used for each row of teeth. This means that the movable bottom plate 30 may be retained in positions having a mutual spacing being smaller than—such as half—the pitch of the row of teeth 33. Thus, such small spacing may be obtained without requiring close tolerances in moulding the row of teeth, while the lengths of pawl members, made for example from metal, may rather exactly be cut to the desired lengths.

In order to facilitate the transportation of sticks and for making it easy for a user to handle the sticks, the sticks are mounted in a cartridge. The section below describes the method of how to load a cartridge with preferably 50 lateral or 100 colorimetric sticks by using a loading device, see FIG. 39-42 for illustration:

The testing devices are stacked and the stack is introduced in the storage container or cassette in the following manner:

A mounting tool (not shown) comprises a base and a pair of upwardly extending guide legs. These legs are dimensioned such as to be received in opposite recesses or cut-outs 35 formed in the testing devices (FIGS. 1-3 and FIGS. 4 and 5, respectively). As a first step, the movable bottom plate 30 is positioned on the base of the tool, where after the desired number of testing devices is stacked on top of the bottom plate such that the guide legs of the mounting tool are received in the opposite recesses 35 of the testing tools. Finally, the tool with the stacked testing devices is inserted into a cassette via the open bottom or bottom opening 37 and pushed towards the flanges or ledges 28. When the pawl members 34 of the bottom plate 30 have come into engagement with the rows of teeth 33, the tool may be withdrawn from the cassette, while the movable bottom plate 30 and the stacked testing devices remains therein, because the pawl members 34 of the bottom plate 30 engage with the corresponding rows of teeth 33 on the inner surfaces of the cassette. As shown in FIG. 9 a longitudinally extending corner guide 36 is formed in each inner corner of the cassette for guiding the complementary shaped corners of the flanges 18 and 23, respectively, of the stacked testing devices when being displaced upwardly through the tubular cassette.

A method useable for loading a cartridge is described below.

Firstly a movable bottom is placed in a temporary fixture between the two guide legs 47. Secondly, a number of lateral or colorimetric sticks are placed in the fixture on top of the movable bottom and also between the two guide legs. The recesses in the end of the stick guide the sticks along the columns, see FIGS. 23 and 24. When the sticks are in place a cartridge is taken down to the fixture and guided so that the two guide legs penetrates the cartridge from the bottom. Preferably the cartridge is pushed downwards until the one-way stairs inside the cartridge gets in contact with the pawls of the movable bottom. In order to get the sticks to the top of the cartridge, the position of the cartridge is secured, while the auxiliary plate of the fixture is being pushed upwards. To secure that the stack of sticks are kept in place, cartridges may preferably be loaded and unloaded in a loading device.

The lifting device (auxiliary plate) in the loading device is preferably at least partly positioned between the two guide legs, and is preferably of the same size or smaller than a testing device. The distance between the first and the second guide leg is adjusted so that a testing device can be guided between the first and second guide legs. The mounting tool and the method are preferably designed so that the loading can be automatically performed.

A cassette of the type shown in FIGS. 6 and 7 loaded with stacked testing devices may be mounted in an automatic analyser such that a spring biased piston or plunger is moved through the bottom opening 37 of the cassette into engagement with the movable bottom plate 30 therein for biasing the stack of testing devices towards the bottom side of the flanges or ledges 28. The cassette may be retained in position by means of oppositely extending mounting pins 38. The upper testing device is retained in position in alignment with the discharge opening 31 by the resilient finger 32 to avoid unintentional discharge. However, the analyser may move the upper testing device into the processing path of the analyser by means of a reciprocating carrier pin of the analyser movable via a funnel-shaped entrance 39 (FIGS. 6 and 7) into the transverse space 29 and into engagement with the upper testing device so as to transfer the same to the processing path of the analyser via the discharge opening 31. When the upper testing device has been discharged from the cassette the stack of testing devices within the cassette will be moved a step upwardly under the influence of the biasing piston or plunger, where after the discharge operation may be repeated. When a testing device has been used for analysing a liquid sample, the device may be discarded or the test member 11, 20 may be removed from the holder 10, 19, where after the holder may be reused together with a fresh test member.

The cassettes shown in FIGS. 6 and 7 may be made from two laterally reversed halves which may be welded or glued together or irreversibly interlocked by mechanical snap locking means. These halves may possibly be integrally moulded such that they are hinge connected along one side.

The cassettes or cartridges shown in FIGS. 6,7,25 and 26 may further comprise a front edge surface 37*a* and a back edge surface 37*b* comprising at least one energy director, shown in FIG. 29. The energy director(s) of the left half front edge surface and back end surface is located in relation to guide ways on the right half front edge surface and back edge surface for receiving the energy director(s). These energy directors facilitate the joint of the two halves during ultrasonic welding.

It should be understood that the projections 15 formed on the holder 10, 19 may be of any shape as long as they are able to allow insertion of the test member 11, 20 into the holder and to retain the test member therein in the desired mutual position. As an example, the projections 15 may be in the form of pins extending obliquely towards the abutment surfaces defined by the walls 13, 22. Furthermore, the projections may be positioned differently spaced from these abutment surfaces so that test members 11, 20 of different thicknesses may be safely retained in one and the same holder 10, 19.

Figure 11:
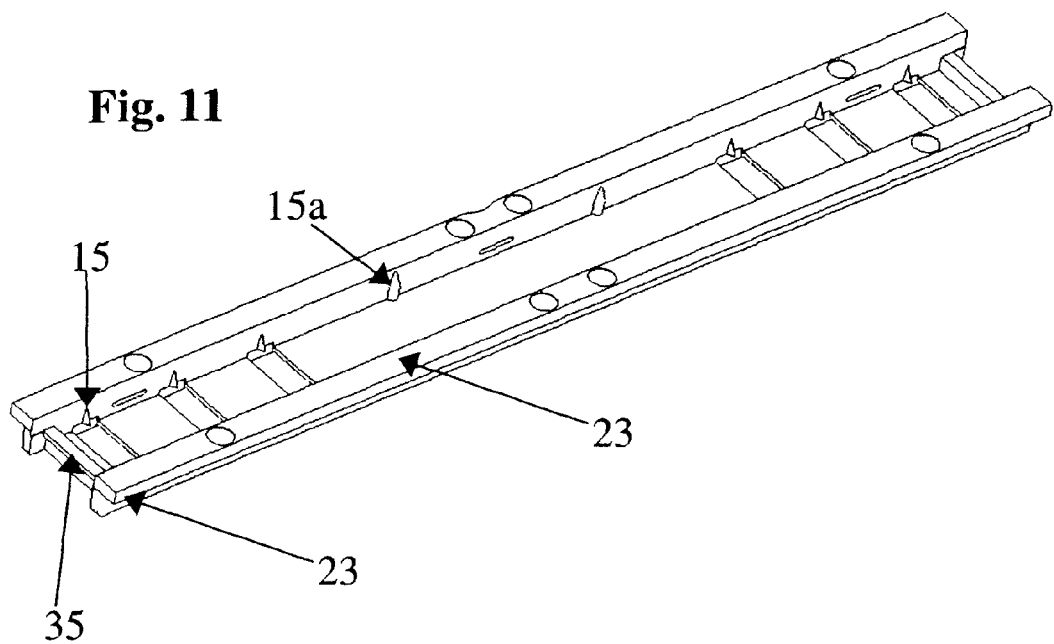
FIG. 11 is a top perspective view of a third embodiment of an empty holder according to the invention.
Figure 12:
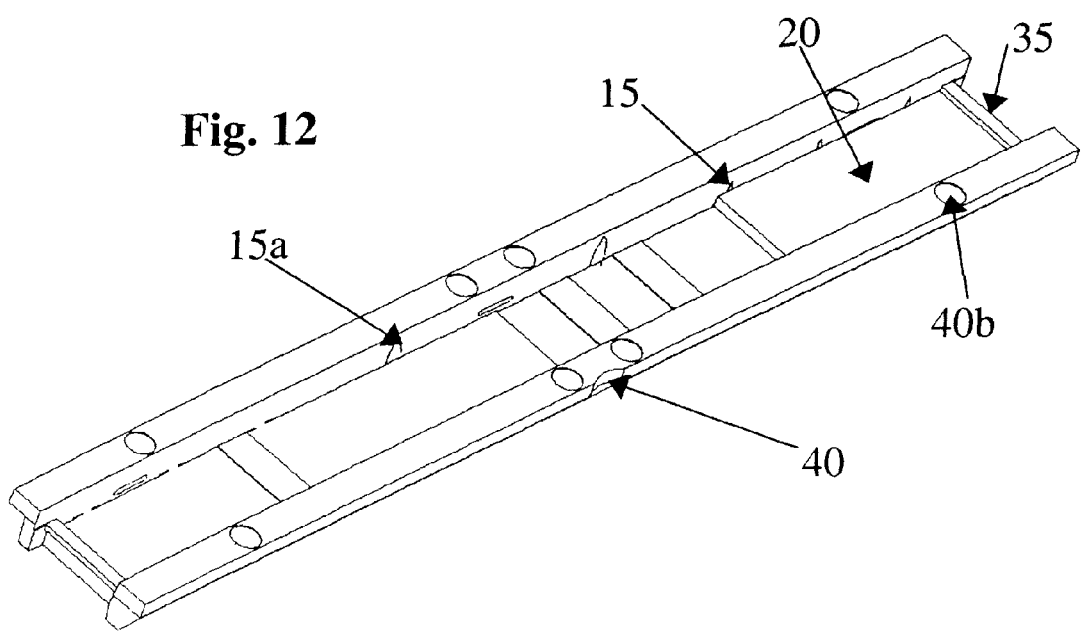
FIG. 12 is a top perspective view of a third embodiment loaded with a test stick.

FIG. 12 illustrates another embodiment of the testing device according to the invention comprising a channel-shaped holder 19 shown in FIGS. 5 and 11 and an elongated strip-type test member 20 having varying thickness along its length. The channel-shaped holder 19 has a pair of opposite side walls 21 and a connecting bottom wall 22 defining an inner abutment surface corresponding to the bottom surface of the upper wall 13 in the embodiment described above in connection with FIGS. 1-3. A number of tooth-like projections 15 corresponding to those described above in connection with FIGS. 1-3 are formed on the opposite inner surfaces of the side walls 21. A pair of oppositely directed flanges 23 extends from the upper edges of the side walls 21 and serves as guide flanges when the testing device is processed in an analyser. A number of rib-shaped projections 15*a* are formed on the opposite inner surfaces of the side walls 21, in order to obtain a better fit of the chemistry in the frame.

Figure 13:
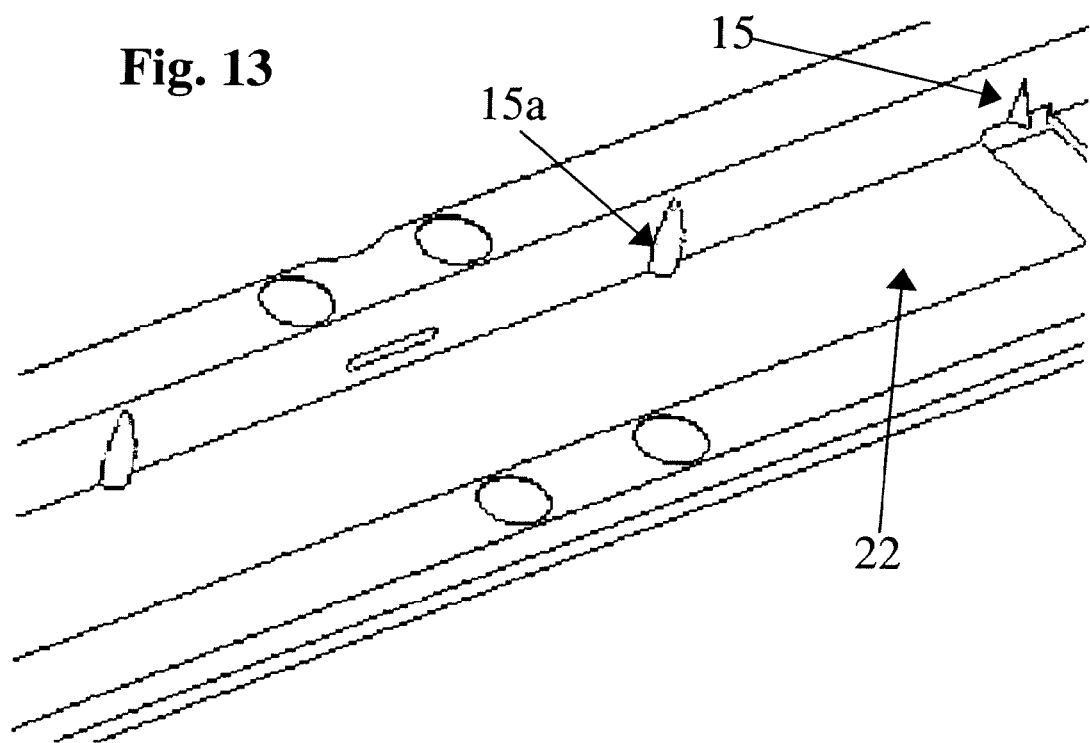
FIGS. 13 and 14 are a magnification of the central part of holder shown in FIGS. 11 and 12, illustrating two rib-shaped protrusions.
Figure 14:
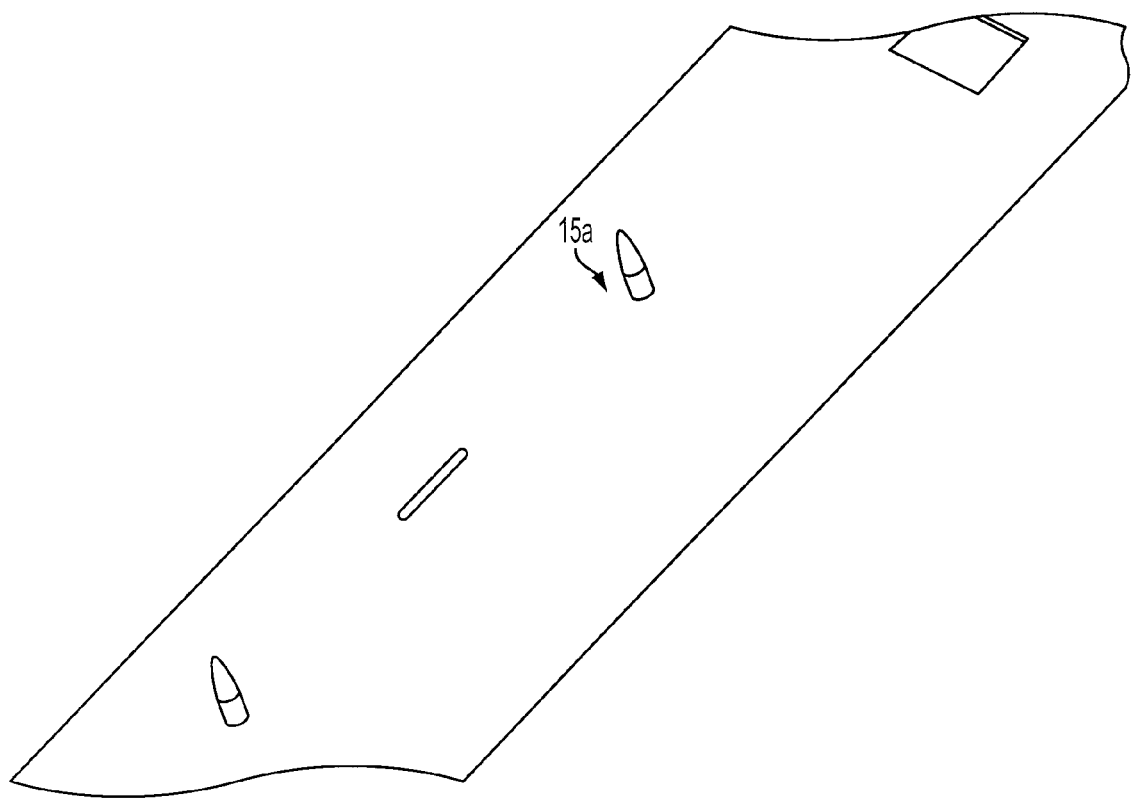
Figure 15:
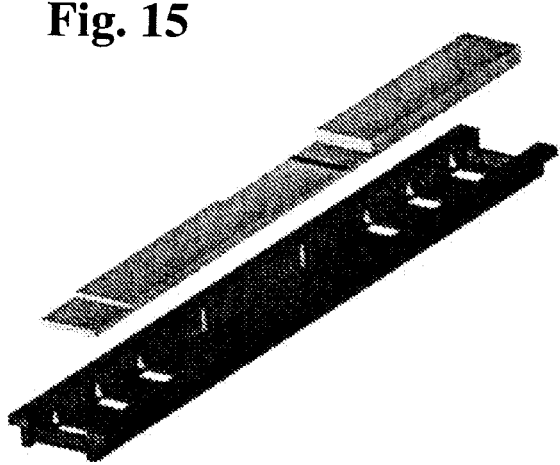
FIG. 15 is a top perspective of a second embodiment of an empty holder with a test stick above.

FIGS. 13 and 14 is a magnification of the holder in FIGS. 11 and 12. These figures illustrates in relation to the bottom wall 22, two vertical ribs 15*a* formed on the opposite inner surface of the side walls FIG. 15 illustrates the holder and test stick shown in FIGS. 11 and 12 but here the stick is separated from the holder.

Figure 16:
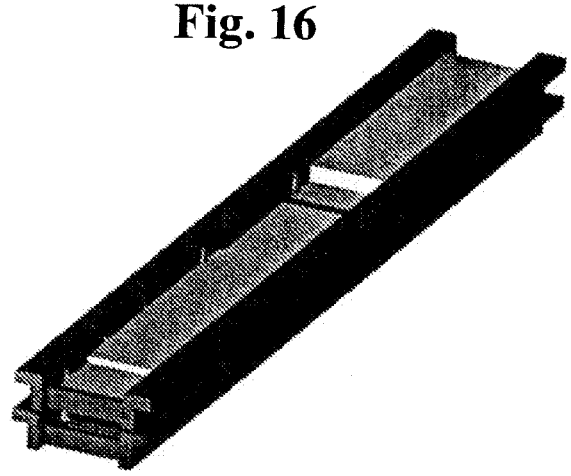
FIG. 16 shows two LS frames piled up.

FIG. 16 illustrates two holders shown in FIGS. 11 and 12, piled on top of each other.

FIGS. 17-20 illustrate another embodiment of a testing device according to the invention comprising a holder 10 and a sheet- or plate-like test carrier or test member 11, which is a sheet or plate member containing for example colorimetric reagents. The holder 10, which may be made from plastic material by injection moulding, and the test sheet member 11 are produced separately and usually at different locations. Therefore, before the testing device may be used the test sheet member has to be mounted in the holder 10.

The holder 10 shown in FIGS. 17-20, comprises a substantially rectangular frame 12 having inner side walls defining a pit having a cross-section corresponding to the size and shape of the test member 11. The bottom of the pit is defined by the frame 12 and is partly covered by a lower wall 22 defining an abutment surface. The top surface of the lower wall 22 defines an abutment surface for the sheet-like test member 11 when mounted in the holder 10.

Oppositely arranged inner side wall parts have tooth-like projections 15 formed thereon. Each projection has a sloping leading edge 16 and a support surface or trailing surface 17, which is opposite to and substantially parallel with the top surface of the lower wall 22. Wing-like flanges 18 extending outwardly from opposite sides of the rectangular frame 12 are used for guiding the testing device along a path of movement or processing path in an automatic analyser, not shown.

A plate or sheet-like test member 11, such as a sheet of chemistry paper with a thickness of about 0.4 mm, may be mounted in the holder shown in FIG. 17-20, simply by pushing the test member downwardly trough the frame 12 towards the top surface of the lower wall 22. The edge portions of the sheet-like test member 11 thereby come into engagement with the leading edges 16 of the projections, whereby these edge portions are locally compressed. Preferably, the thickness of the test member 11 corresponds to the axial distance between the abutment surface formed by the top surface of the lower wall 22 and the opposite supporting surfaces 17 of the projections 15. In such case the test member may be safely retained in position in the holder 10 between the top surface of the wall 22 and the opposing supporting surfaces 17 of the projections 15. When the testing device has been introduced into an analyser a liquid sample to be tested may be applied to the surface of the test member 11, and a colorimetric reaction may be read by the analyser and translated into a test result.

Figure 21:
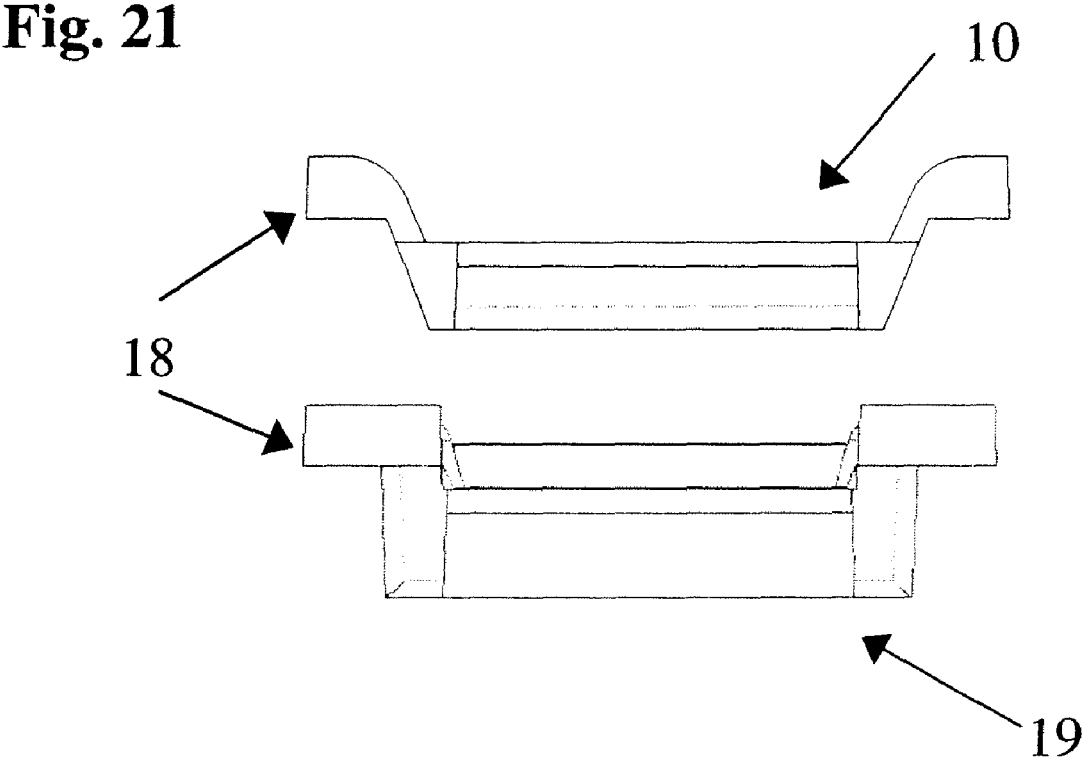
FIG. 21 is a profile view of the embodiments one to four, according to the invention.

FIG. 21 shows the two different types of frames 10 and 19, in profile. The frames have wing-like flanges 18 extending outwardly from opposite sides of the rectangular frame 12 used for guiding the testing device along a path of movement or processing path in an automatic analyser, not shown.

Figure 22:
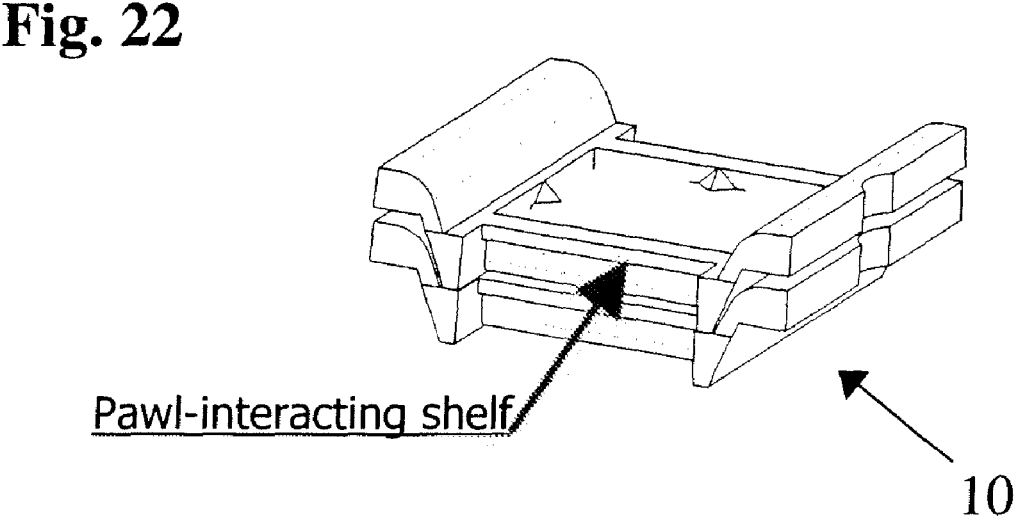
FIG. 22 shows two frames piled up on top of each other.

FIG. 22 illustrates two holders shown in FIG. 1-3 or 17-20, piled on top of each other.

FIG. 23 shows the drawings of the third embodiments.

FIG. 24 shows the drawings of the fourth embodiment.

Figure 25:
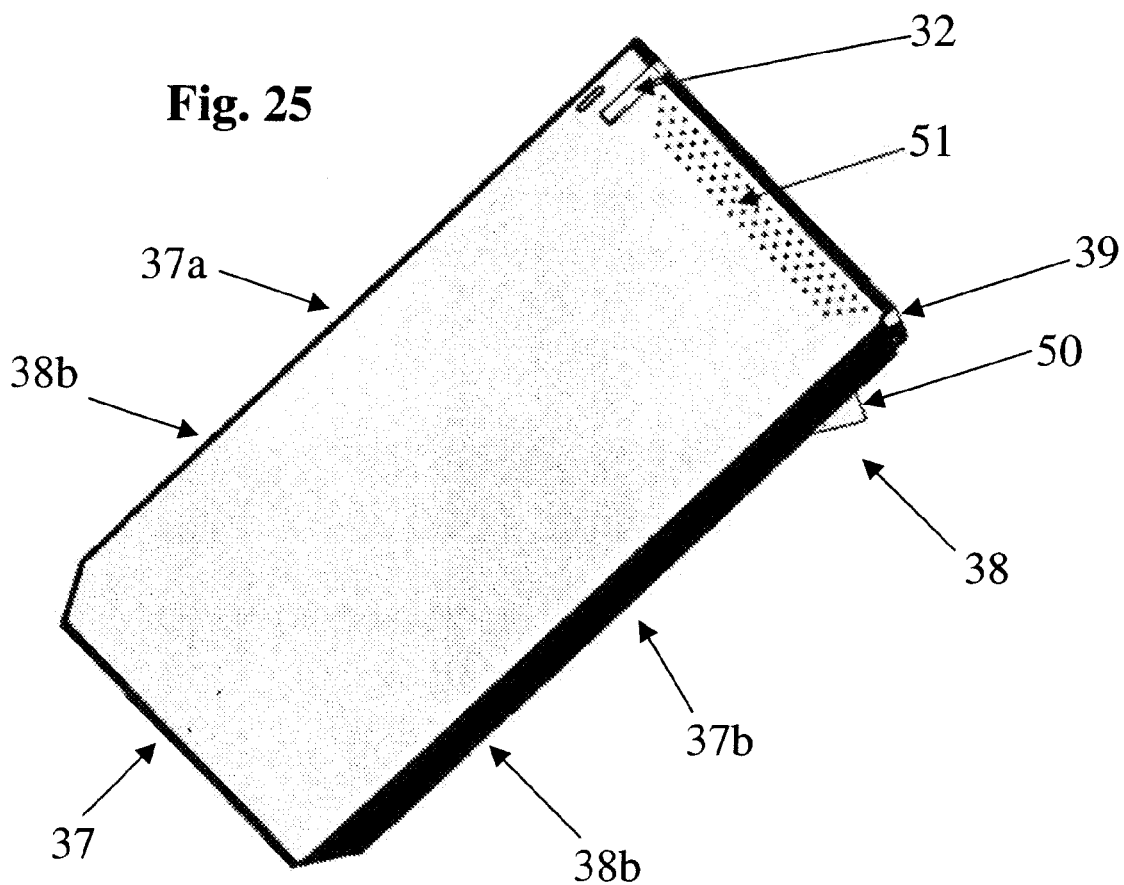
FIG. 25 is a perspective view of a third embodiment of a storage container or cassette according to the invention for receiving a stack of testing devices as shown in FIGS. 5, 11 and 12.

FIG. 25 shows a side view of a cartridge for the holder 19. The cartridge has a resilient finger 32, for preventing the stick holder to fall out during transportation of the cartridge. Also the cartridge has grip protrusions 51 on the upper half of the sides for increasing the friction between the hand and the cartridge when loading and unloading the cartridge. Furthermore the cartridge also has a external protrusion 38 located on the back surface in the vicinity of the upper discharge opening, on the same edge as the funnel-shaped entrance 39. The protrusion has an abutment surface 50.

Figure 26:
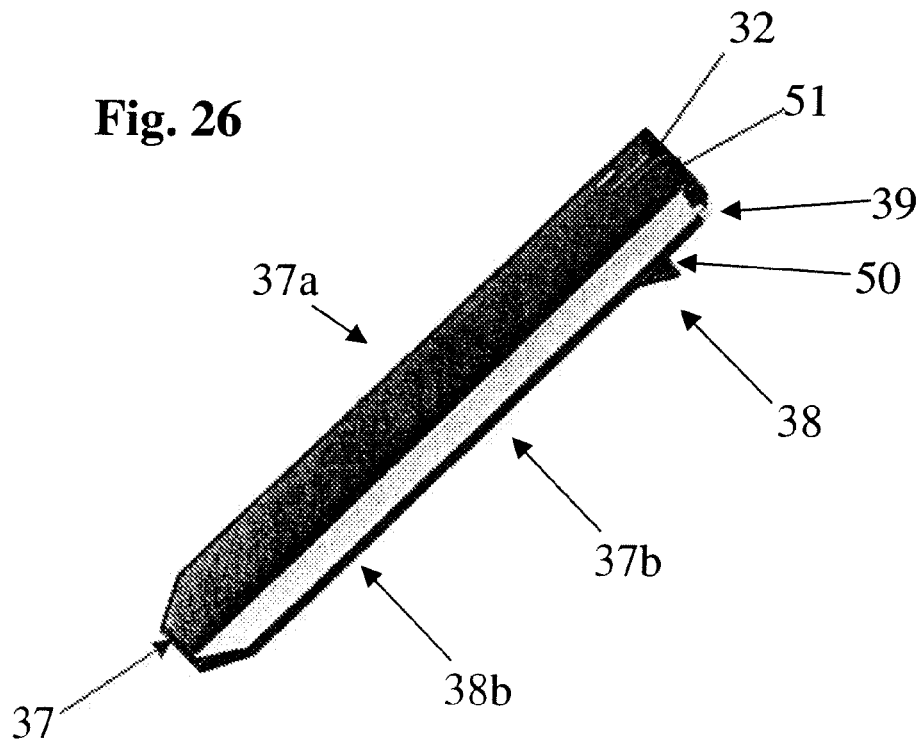
FIG. 26 is a perspective view of a fourth embodiment of a storage container or cassette according to the invention for receiving a stack of testing devices as shown in FIGS. 2, 3, and 19.

FIG. 26 shows a side view of a cartridge for the holder 10. The cartridge has a resilient finger 32, for preventing the stick holder to fall out during transportation of the cartridge. The cartridge has grip protrusions on the upper half of the sides for increasing the friction between the hand and the cartridge when loading and unloading the cartridge. The cartridge also has a protrusion 38 on the same edge as the funnel-shaped entrance 39. The protrusion has an abutment surface 50, for providing a preferred vertical storage positioning during storage of the cartridge in the analysis instrument (not shown). The cartridge further comprises a hole, 38b in the wall 37b as well as in the wall 37a. These holes are preferably adopted for receiving retaining means (Not shown) for holding the cartridge in a loading position when the cartridge is being loaded in to an analysis instrument (Not shown). Thus facilitating the loading for a user.

FIG. 27 shows two cross-sections of the cartridge for the holder 10, the above cross-section shows the cartridge before assembly 27a and the lower cross-section show the cartridge after it is assembled 27b. The corner guide 36 and the rows of teeth or ratchet teeth 33 can also be seen.

FIG. 28 shows a magnification of the energy directors whereby the two cartridge halves are welded together by preferably ultrasonic welding.

FIG. 29 shows one of the halves of a cartridge for the holder 19, with three energy directors 52.

Figure 30:
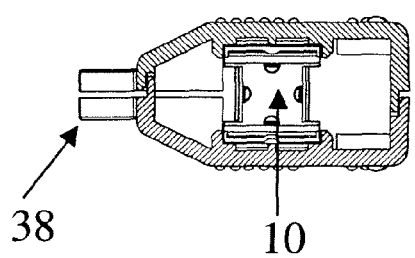
FIG. 30 shows a cross-section of an assembled cartridge having a test slide inside.

FIG. 30 shows a cross-section of a cartridge wherein a holder 10 is placed. Furthermore the abutment surface 50 of the protrusion 38 can be seen.

Figure 31:
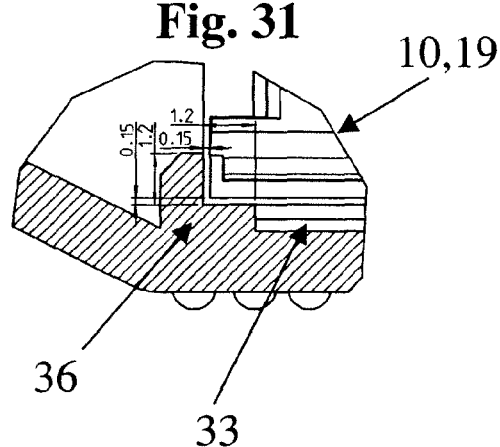
FIG. 31 shows a magnification of the corner guides.

FIG. 31 shows a magnification of the grip protrusions 51, corner guide 36 and of the rows of teeth or ratchet teeth 33.

Figure 32:
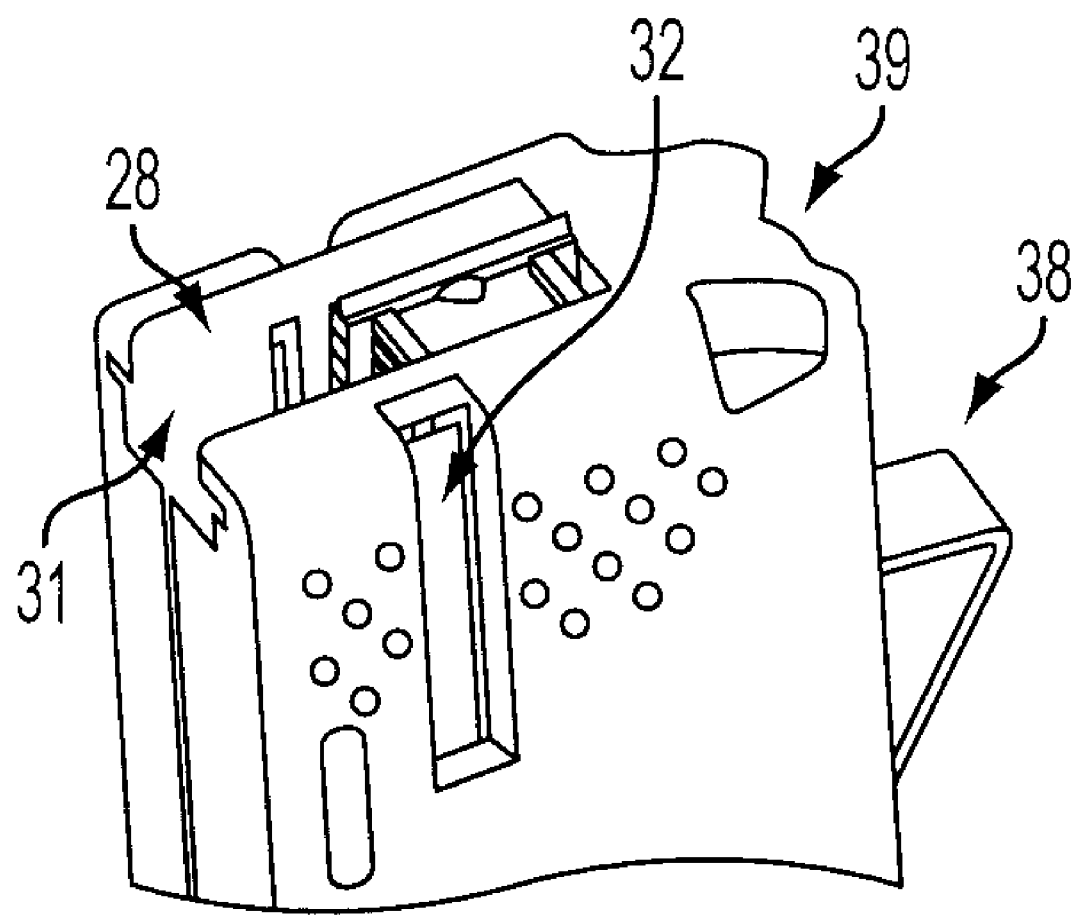
FIG. 32 shows the top part of a cartridge according to the fourth embodiment.

FIG. 32 shows a close up of the upper part of a cartridge illustrating the preferred placement of a resilient finger 32.

Figure 33:
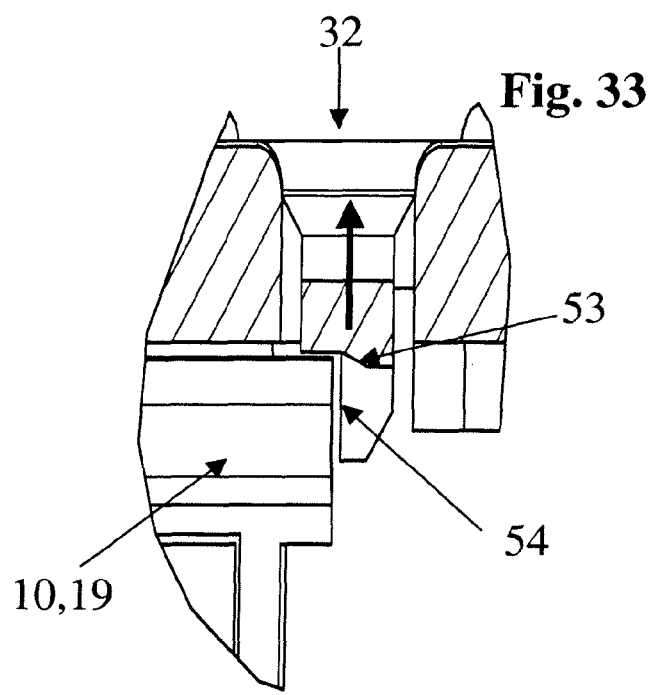
FIG. 33 shows a cross-section of the resilient finger.
Figure 34:
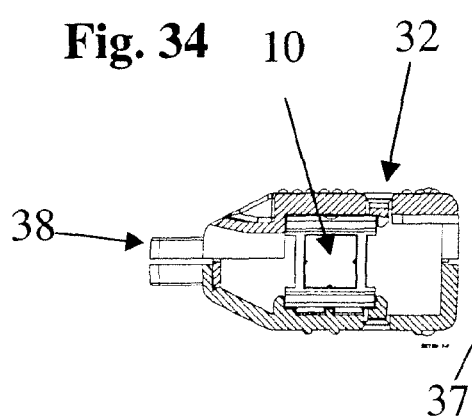
FIG. 34 shows a cross-section of a cartridge according to the fourth embodiment.

FIGS. 33 and 34 shows a cross-section of the resilient finger, wherein the sloping abutment surface 53 for preventing holders to fall out during transportation of the cartridge but at the same time has the feature to release a holder when the holder is pushed against the resilient finger. The resilient finger further comprises a second level abutment surface 54, abutting the holders below the upper holder.

Figure 35:
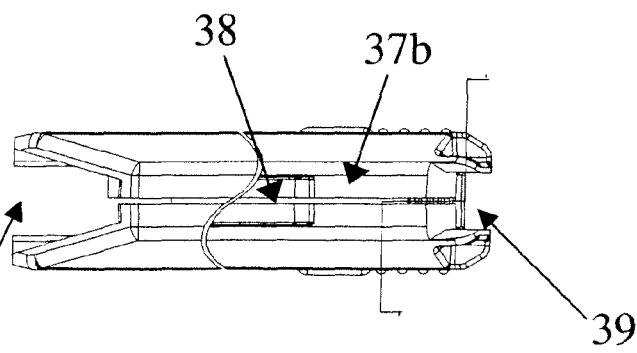
FIG. 35 shows an edge view of a cartridge.

FIG. 35 shows a cartridge with the funnel-shaped entrance 39.

FIG. 36 shows two embodiments of the movable bottom plate having a support surface comprising a stick support side 41 and a plunger abutment side 42. The bottom plate further comprising four legs 43 having a base area 46 and a pawl area 34. Furthermore the bottom plate comprises a slope 44 in one of the end for guiding a stick remover pawl.

Figure 37:
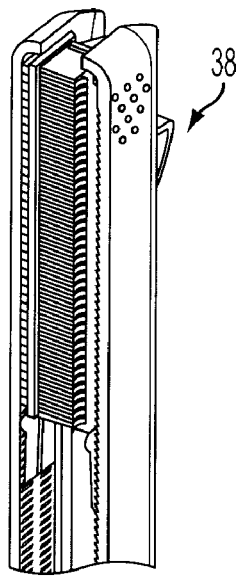
FIG. 37 shows a cartridge loaded with holders.
Figure 38:
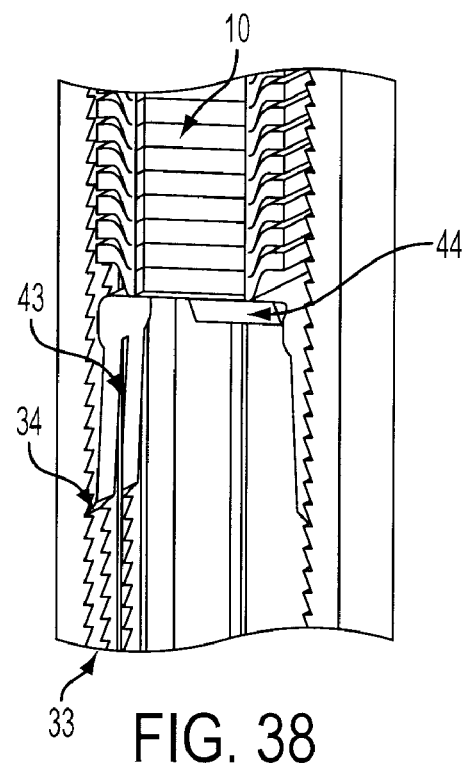
FIG. 38 is a magnification of the mounting of a movable bottom plate.
Figure 39:
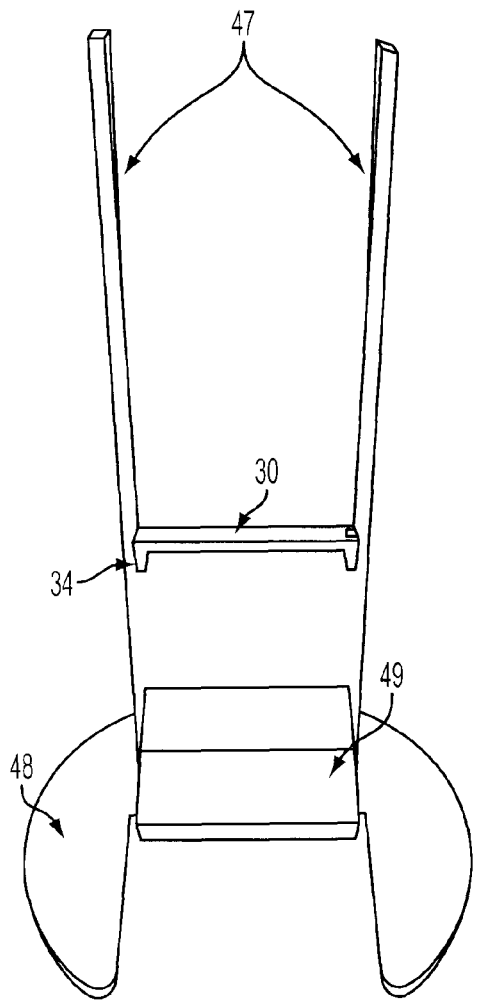
FIG. 39 shows a mounting tool for loading cartridges.
Figure 40:
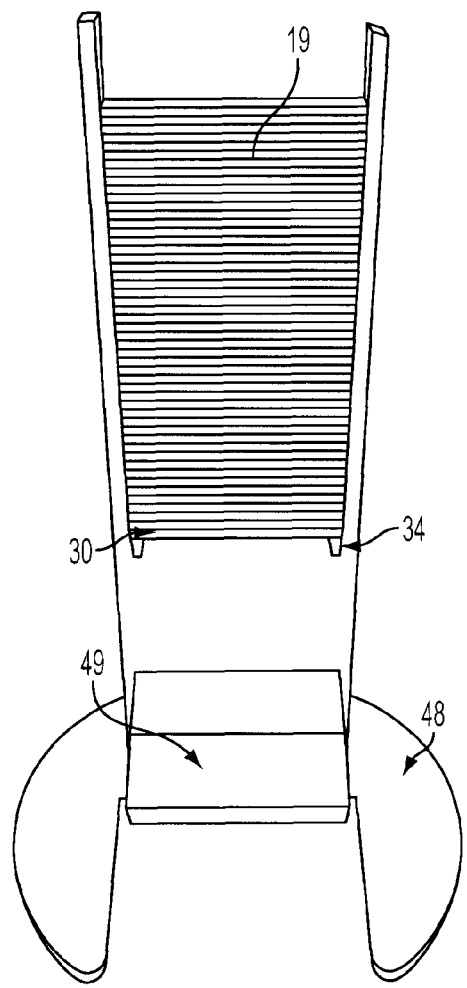
FIG. 40 shows holders piled-up in the mounting tool or loading device.
Figure 41:
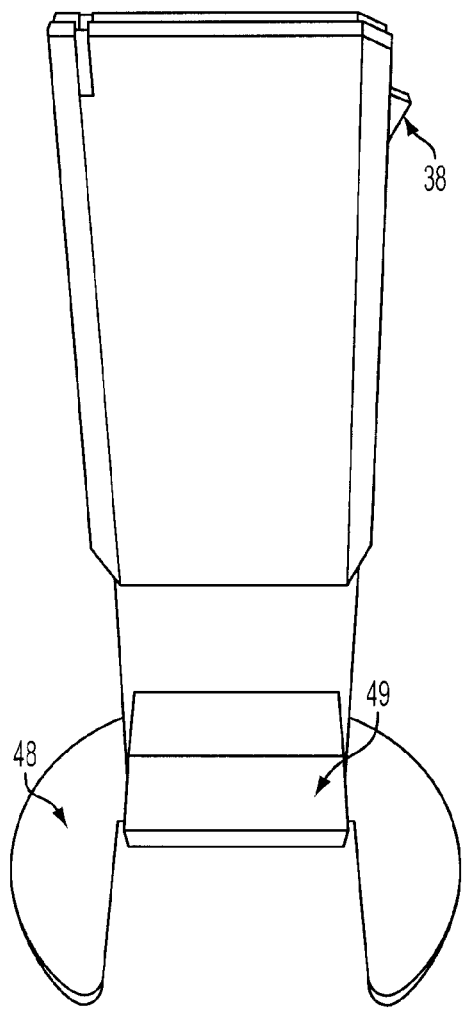
FIG. 41 shows a cartridge placed over the sticks and the two guiding legs of the mounting tool. Furthermore a lifting device is shown in this figure.
Figure 42:
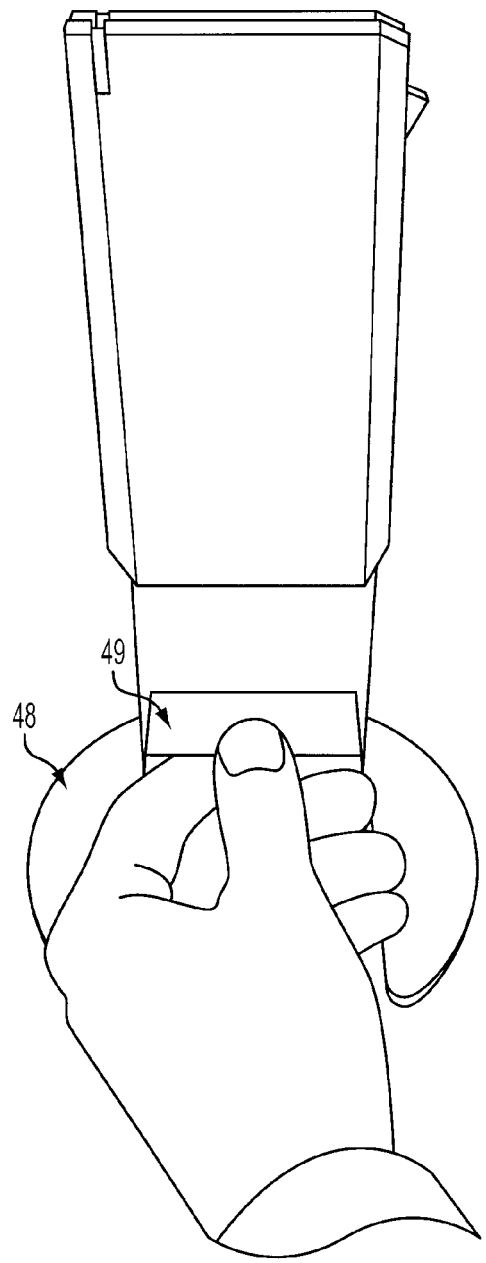
FIG. 42 shows the same as FIG. 41, with the lifting device in a raised position.

FIGS. 37 and 38 shows a cartridge for holders (10), wherein the placement of sticks and the movable bottom plate can be seen.

FIG. 39-42 shows a mounting tool for loading cartridges with holders. The mounting tool comprises a pair of upwardly extending guide legs 47 and a base 48. The mounting tool further comprises a lifting device 49 for pushing the stack of holders towards the flanges 28 and for forcing the floating bottom plate into the cartridge so that the pawl area 34 of the legs of the bottom plate gets in contact with the rows of teeth or ratchet teeth 33 on the inside of the cartridge.

The invention claimed is:

1. A testing device for testing or analysing fluids comprising:
    at least one sheet-or plate-like test member including analysis reagent and having opposite side surfaces surrounded by edge portions, and
    a separately produced holder having retaining means for receiving and retaining the test member in a predetermined relative position in the holder,
    said retaining means comprising an abutment surface engaging with one of said side surfaces of the test member and projections, which are positioned and shaped so as to allow insertion of the test member into the holder by moving the test member into engagement with said abutment surface while engaging with opposite edge portions of the test member, and said holder having upper and lower complementary surfaces so as to allow stacking of a plurality of testing devices on top of each other, which complementary surfaces are shaped so as to allow mutual displacement of stacked testing devices along one axis transversely to a longitudinal direction of the stack and prevent mutual displacement of stacked testing devices along other axes transversely to the longitudinal direction of the stack.

2. A testing device according to claim 1, wherein the projections are tooth-shaped with pointed ends.

3. A testing device according to claim 1, wherein at least some of the projections have a leading edge forming a ramp sloping towards a plane defined by the abutment surface so as to facilitate insertion of the test member into the holder.

4. A testing device according to claim 1, wherein at least some of the projections have a trailing edge or surface extending substantially parallel with and spaced from a plane defined by the abutment surface.

5. A testing device according to claim 1, wherein the projections are positioned so as to be differently spaced from a plane defined by the abutment surface.

6. A testing device according to claim 1, wherein the holder is a channel-shaped member having an inner bottom surface defining said abutment surface and opposite inner side surfaces from which the projections extend in opposite directions.

7. A testing device according to claim 1, wherein the test member is an elongated test member of the "lateral flow stick" type, in which the fluid to be tested is supplied at one end of the elongated test member.

8. A testing device according to claim 1, wherein the holder is frame-shaped and defines an opening therein, the abutment surface extending around and adjacent to said opening.

9. A testing device according to claim 1 for use in colorimetric testing of milk.

10. A testing device according to claim 1, wherein the holder further comprises an upper side and a lower side in relation to an analysis instrument, and wherein the retaining means are positioned and shaped so as to allow insertion of the test member in to the holder from the upper side.

11. A holder comprising means for receiving and retaining a sheet-or plate-like test member, which has opposite side surfaces surrounded by edge portions, in a predetermined relative position in the holder, said retaining means comprising an abutment surface for engaging with one of said side surfaces of the test member and projections, which are positioned and shaped so as to allow insertion of the test member into the holder by moving the test member into engagement with said abutment surface while engaging with opposite edge portions of the test member, said holder having upper and lower complementary surfaces so as to allow stacking of a plurality of testing devices on top of each other, which complementary surfaces are shaped so as to allow mutual displacement of stacked testing devices along one axis transversely to a longitudinal direction of the stack and prevent mutual displacement of stacked testing devices along other axes transversely to the longitudinal direction of the stack.

12. A holder according to claim 11, wherein the projections are tooth-shaped with pointed ends.

13. A holder according to claim 11, wherein at least some of the projections have a leading edge forming a ramp sloping towards a plane defined by the abutment surface so as to facilitate insertion of the test member into the holder.

14. A holder according to claim 11, wherein at least some of the projections have a trailing edge or surface extending substantially parallel with and spaced from a plane defined by the abutment surface.

15. A holder according to claim 11, wherein the projections are positioned so as to be differently spaced from a plane defined by the abutment surface.

16. A holder according to claim 11, wherein the holder is a channel-shaped member having an inner bottom surface defining said abutment surface and opposite inner side surfaces from which the projections extend in opposite directions.

17. A holder according to claim 11, wherein the holder is frame-shaped and defines an opening therein, the abutment surface extending around and adjacent to said opening.

18. A holder according to claim 11, wherein the holder has been integrally formed.

19. A holder according to claim 11, wherein the holder further comprises an upper side and a lower side in relation to an analysis instrument, and wherein the retaining means are positioned and shaped so as to allow insertion of the test member in to the holder from the upper side.

20. A cartridge for receiving, storing and unloading a plurality of stacked testing devices, the cartridge comprising:
 a housing defining an internal passage containing a stack of testing devices, wherein a testing device in the stack of testing devices comprises:
  at least one sheet-or plate-like test member including analysis reagent and having opposite side surfaces surrounded by edge portions, and
  a separately produced holder having retaining means for receiving and retaining the test member in a predetermined relative position in the holder,
 said retaining means comprising an abutment surface engaging with one of said side surfaces of the test member and projections, which are positioned and shaped so as to allow insertion of the test member into the holder by moving the test member into engagement with said abutment surface while engaging with opposite edge portions of the test member, and said holder having upper and lower complementary surfaces so as to allow stacking of a plurality of testing devices on top of each other, which complementary surfaces are shaped so as to allow mutual displacement of stacked testing devices along one axis transversely to a longitudinal direction of the stack and prevent mutual displacement of stacked testing devices along other axes transversely to the longitudinal direction of the stack,
 said housing comprising:
  a lower charge opening for receiving said stack of testing devices,
  a support member for supporting a lower testing device in said stack,
  an upper abutment surface for engaging with an upper testing device in the stack, and
  an upper discharge opening, substantially aligned with said upper testing device, so as to allow discharge of said upper testing device by displacing the same along said abutment surface.

21. A cartridge according to claim 20, wherein the housing is assembled by two halves, together defining oppositely side surfaces, and a front and a back surface.

22. A cartridge according to claim 21, wherein the two halves are detachable or non-detachably assembled.

23. A cartridge according to claim 20, wherein at least the discharge opening comprises guiding trails or incisions for guiding a testing device upon discharging.

24. A cartridge according to claim 21, wherein the side surfaces comprise guiding trails for guiding said stack of testing devices through the passage.

25. A cartridge according to claim 21, wherein the side surfaces further comprise at least one serrated track on the inside, forming one side of an internal one-way stair for a support member.

26. A cartridge according to claim 20, wherein the support member is movable in relation to the housing.

27. A cartridge according to claim 26, further comprising one-way means associated with the movable support member allowing the movable support member to move in a direction towards the upper abutment surface, only.

28. A cartridge according to claim 27, wherein said one-way means comprise at least one succession of teeth, such as a rack or ratchet teeth, and at least one pawl member cooperating therewith.

29. A cartridge according to claim 20, comprising at least two pawl members, which are connected to the supporting member for co-operating with a succession of teeth formed on an inner side surface of a storage container, wherein free ends of the pawl members are spaced in a longitudinal direction of the container by a distance being different from a multiple of a pitch of the succession of teeth, preferably smaller than said pitch.

30. A cartridge according to claim 21, wherein at least one of the side surfaces further comprises a locking device in the vicinity of the discharge opening, for preventing unintentional discharges of testing devices.

31. A cartridge according to claim 30, wherein the locking device comprises at least one flexible protrusion obstructing at least a part of said discharge opening.

32. A cartridge according to claim 20, further comprising an external protrusion for abutting a support surface on a storage carousel in an analysis instrument.

\* \* \* \* \*